United States Patent
Roveda et al.

(10) Patent No.: US 12,310,758 B2
(45) Date of Patent: May 27, 2025

(54) NEURAL-NETWORK BASED ELECTROCARDIOGRAMY MONITOR AND ASSOCIATED METHODS

(71) Applicant: ARIZONA BOARD OF REGENTS OF THE UNIVERSITY OF ARIZONA, A BODY CORPORATE, Tucson, AZ (US)

(72) Inventors: Janet Roveda, Tucson, AZ (US); Siteng Chen, Tucson, AZ (US); Ao Li, Tucson, AZ (US); Stuart Quan, Tucson, AZ (US); Linda Powers, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 941 days.

(21) Appl. No.: 17/363,933

(22) Filed: Jun. 30, 2021

(65) Prior Publication Data
US 2021/0401376 A1 Dec. 30, 2021

Related U.S. Application Data

(60) Provisional application No. 63/046,504, filed on Jun. 30, 2020.

(51) Int. Cl.
| | | |
|---|---|---|
| *G06N 3/02* | (2006.01) | |
| *A61B 5/00* | (2006.01) | |
| *A61B 5/346* | (2021.01) | |
| *G06N 3/044* | (2023.01) | |
| *G06N 3/045* | (2023.01) | |
| *G06N 3/063* | (2023.01) | |

(52) U.S. Cl.
CPC ............ *A61B 5/7264* (2013.01); *A61B 5/346* (2021.01); *A61B 5/7285* (2013.01); *G06N 3/02* (2013.01); *G06N 3/044* (2023.01); *G06N 3/045* (2023.01); *G06N 3/063* (2013.01)

(58) Field of Classification Search
None
See application file for complete search history.

(56) References Cited

U.S. PATENT DOCUMENTS

| | | | |
|---|---|---|---|
| 2018/0144465 A1* | 5/2018 | Hsieh ...................... | G06N 3/04 |
| 2019/0090774 A1* | 3/2019 | Yang ...................... | A61B 5/303 |
| 2019/0236454 A1* | 8/2019 | Fok ........................ | G06N 3/084 |

(Continued)

OTHER PUBLICATIONS

Pillar G, Bar A, Shlitner A, Schnall R, Shefy J, Lavie P. Autonomic arousal index: an automated detection based on peripheral arterial tonometry. Sleep. 2002.

(Continued)

*Primary Examiner* — Xuyang Xia
(74) *Attorney, Agent, or Firm* — Cozen O'Connor

(57) ABSTRACT

Systems and methods detect cortical arousal events from a single time-varying ECG signal that is obtained via single-lead ECG. A pre-trained deep neural network transforms the ECG signal into a sequence of cortical-arousal probabilities. The deep neural network includes an inception module, a residual neural network, and a long short-term memory neural network to identify structure in the ECG signal that distinguishes periods of cortical arousal from periods without cortical arousal.

18 Claims, 18 Drawing Sheets

(56) References Cited

U.S. PATENT DOCUMENTS

| | | | | |
|---|---|---|---|---|
| 2020/0197656 A1* | 6/2020 | Molina | ................ | A61B 5/4812 |
| 2020/0356846 A1* | 11/2020 | Saripalli | ................ | G06N 3/045 |
| 2021/0106240 A1* | 4/2021 | Kerman | ................ | A61B 5/366 |
| 2021/0118566 A1* | 4/2021 | Wang | ...................... | G06N 3/08 |

OTHER PUBLICATIONS

Pillar G, Bar A, Betito M, et al. An automatic ambulatory device for detection of AASM defined arousals from sleep: the WP100. Sleep Med. 2003;4(3):207-212. doi:10.1016/S1389-9457(02)00254-X.

Basner M, Griefahn B, Müller U, Plath G, Samel A. An ECG-based algorithm for the automatic identification of autonomic activations associated with cortical arousal. Sleep. 2007. doi:10.1093/sleep/30.10.1349.

Olsen M, Schneider LD, Cheung J, et al. Automatic, electrocardiogramased detection of autonomic arousals and their association with cortical arousals, leg movements, and respiratory events in sleep. Sleep. 2018. doi:10.1093/sleep/zsy006.

Hannun AY, Rajpurkar P, Haghpanahi M, et al. Cardiologist-level arrhythmia detection and classification in ambulatory electrocardiograms using a deep neural network. Nat Med. 2019;25(1):65-69. doi:10.1038/s41591-018-0268-3.

Zhang L, Fabbri D, Upender R, Kent D. Automated Sleep Stage Scoring of the Sleep Heart Health Study Using Deep Neural Networks. Sleep. Jul. 2019. doi:10.1093/sleep/zsz159.

Howe-Patterson M, Pourbabaee B, Benard F. Automated Detection of Sleep Arousals From Polysomnography Data Using a Dense Convolutional Neural Network. signal. 2018;1:2.

\* cited by examiner

NEURAL-NETWORK BASED ELECTROCARDIOGRAMY MONITOR AND ASSOCIATED METHODS

RELATED APPLICATIONS

This application claims priority to U.S. Provisional Patent Application No. 63/046,504, filed Jun. 30, 2020, the entirety of which is incorporated herein by reference.

STATEMENT REGARDING FEDERALLY SPONSORED RESEARCH OR DEVELOPMENT

This invention was made with government support under Grant Nos. 1918797 and 1433185, awarded by NSF. The government has certain rights in the invention.

BACKGROUND

The arousal index is an important indicator describing the quality of sleep during diagnostic polysomnography (PSG). Frequent cortical arousals during sleep can cause sleep fragmentation, poor sleep quality, and insufficient sleep. Furthermore, they are associated with a wide range of negative outcomes, such as daytime sleepiness, obesity, cardiovascular dysfunction, and hypertension. Additionally, sleep-disordered breathing (SDB) and periodic leg movements (PLM) increase the frequency of cortical arousal.

SUMMARY

Arousal scoring is particularly important in the identification of hypopnea events observed with sleep-disordered breathing (SDB). According to the American Academy of Sleep Medicine (AASM), the recommended definition of a hypopnea requires a 3% oxygen desaturation from pre-event baseline or an associated cortical arousal. Home sleep testing (HST) is one technique for evaluating possible SDB. However, most Type III sleep monitor systems commonly used for HST cannot detect arousals because they do not monitor the electroencephalogram (EEG). AASM scoring rules define an arousal as an abrupt change in EEG frequency that lasts at least three seconds. Therefore, most HST systems potentially underestimate the apnea-hypopnea index, resulting in some falsely negative studies.

The present embodiments include systems and methods that detect cortical arousal events from a single time-varying ECG signal that is advantageously obtained via single-lead ECG. The embodiments use a pre-trained deep neural network to transform the ECG signal into a sequence of cortical-arousal probabilities. The deep neural network may include several multi-layer convolutional neural networks that identify structure in the ECG signal to distinguish cortical arousal from periods without cortical arousal.

In some embodiments, the deep neural network is repeatedly executed as the ECG signal is recorded, and can thereby be used to provide a "real-time" indicator of cortical arousal. These embodiments may be incorporated into existing patient monitors to add cortical-arousal detection as part of the data displayed to a health-care provider. In other embodiments, the ECG signal is received from a separate, or third-party ECG monitor. For example, the ECG signal may be downloaded from a Holter monitor used to record the ECG signal overnight. In this case, the deep neural network is used for "offline" processing of the ECG signal (i.e., after the ECG signal is fully acquired) to identify periods of cortical arousal.

In embodiments, an electrocardiography (ECG) monitor includes a processor and a memory communicably coupled with the processor. The memory stores a deep neural network and machine-readable instructions that, when executed by the processor, control the ECG monitor to (i) filter, with an inception module of the deep neural network, a sequence of ECG values into a channel array, (ii) downsample, with a residual neural network of the deep neural network, the channel array into a downsampled channel array, (iii) calculate, with a long short-term memory (LSTM) neural network of the deep neural network, a sequence of cortical-arousal probabilities based on the downsampled channel array, and (iv) output the sequence of cortical-arousal probabilities.

In other embodiments, an ECG method includes filtering, with an inception module of a deep neural network, a sequence of ECG values into a channel array. The ECG method also includes downsampling, with a residual neural network of the deep neural network, the channel array into a downsampled channel array. The ECG method also includes calculating, with a LSTM neural network of the deep neural network, a sequence of cortical-arousal probabilities based on the downsampled channel array. The ECG method also includes outputting the sequence of cortical-arousal probabilities.

DETAILED DESCRIPTION

Figure 1:
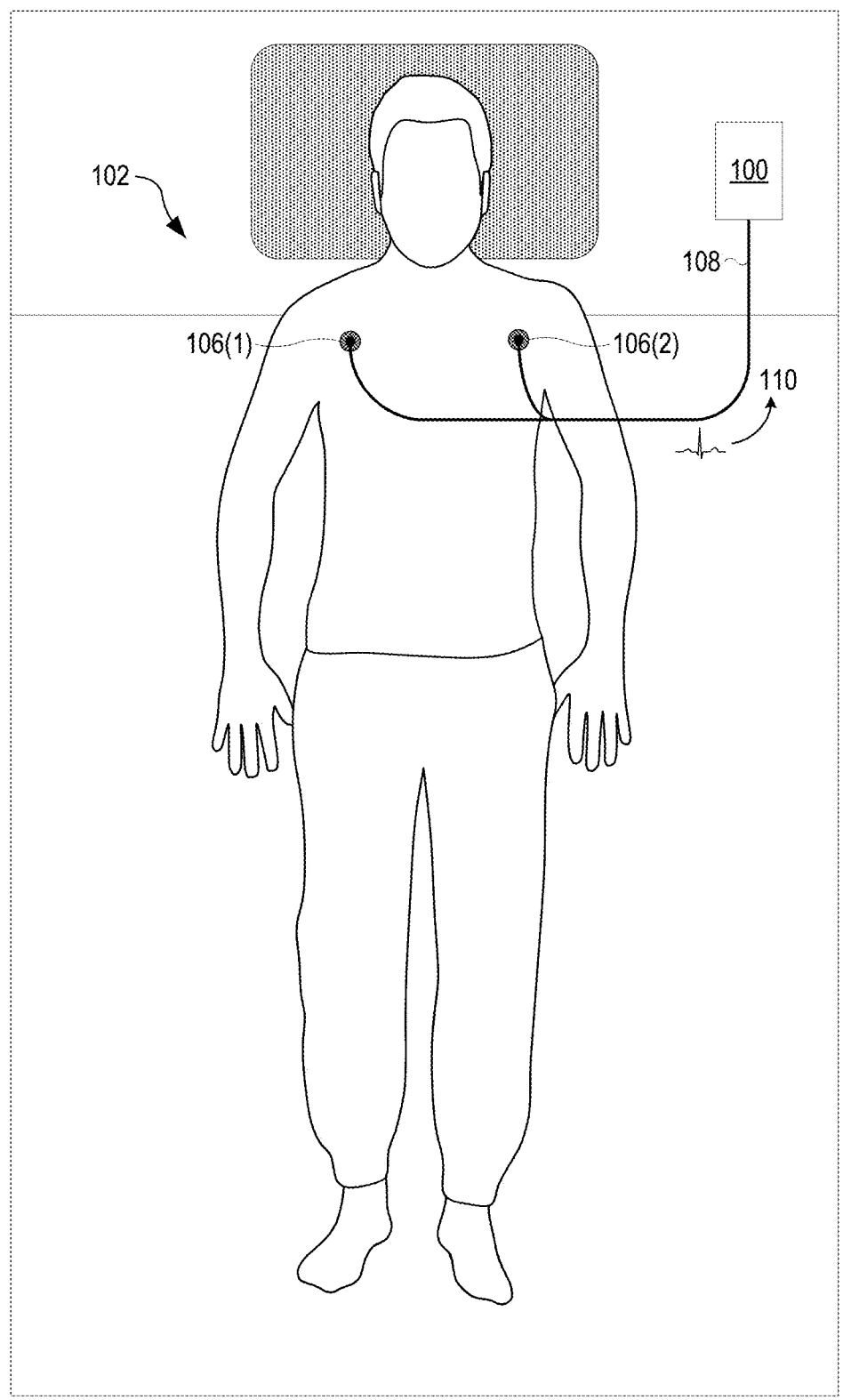
FIG. 1 shows an electrocardiography (ECG) monitor processing an ECG signal to detect cortical arousal during sleep, in an embodiment.

FIG. 1 shows an electrocardiography (ECG) monitor 100 processing an ECG signal 110 to detect cortical arousal during sleep. The ECG monitor 100 obtains the ECG signal 110 by measuring the electric potential difference (i.e., voltage difference) between first and second electrodes 106(1), 106(2) affixed to a person 102. The electric potential at various positions on the person's body, including at the first and second electrodes 106(1) and 106(2), result from activity of the person's heart (e.g., depolarization and repolarization). Thus, FIG. 1 shows an example of single-lead ECG. While the example of FIG. 1 shows the electrodes 106(1) and 106(2) affixed to the chest of the person 102, one or both of the electrodes 106(1) and 106(2) may be affixed elsewhere on the person 102 without departing from the scope hereof. The electrodes 106(1) and 106(2) may also be part of a larger plurality of electrodes used for multi-lead ECG (e.g., ten electrodes 106 used for 12-lead ECG).

The ECG monitor 100 receives the ECG signal 110 from the electrodes 106(1) and 106(2) via an electrical cable 108. In the example of FIG. 1, the ECG signal 110 is an analog signal that the ECG monitor 100 processes and digitizes into an ECG sequence (see the ECG sequence 202 in FIG. 2). The ECG sequence is a list of digital values that are temporally ordered based on when they were sampled from the analog ECG signal 110. Thus, each value of the ECG sequence has a corresponding time at which it was measured. Typically, the ECG signal 110 is sampled regularly at a sampling frequency $f_s$, in which case a time spacing $\Delta t_s$ between sequentially sampled values is $\Delta t_s = 1/f_s$. The ECG monitor 100 processes the ECG sequence to identify periods of cortical arousal, as described in more detail below. For clarity in FIG. 1, the ECG monitor 100 is shown next to the person 102. However, the ECG monitor 100 may be alternatively worn by the person 102 as a Holter monitor. For example, the ECG monitor 100 may be strapped around the torso of the person 102, worn around the neck of the user 102 (e.g., like a necklace), or taped to the stomach of the person 102.

Figure 2:
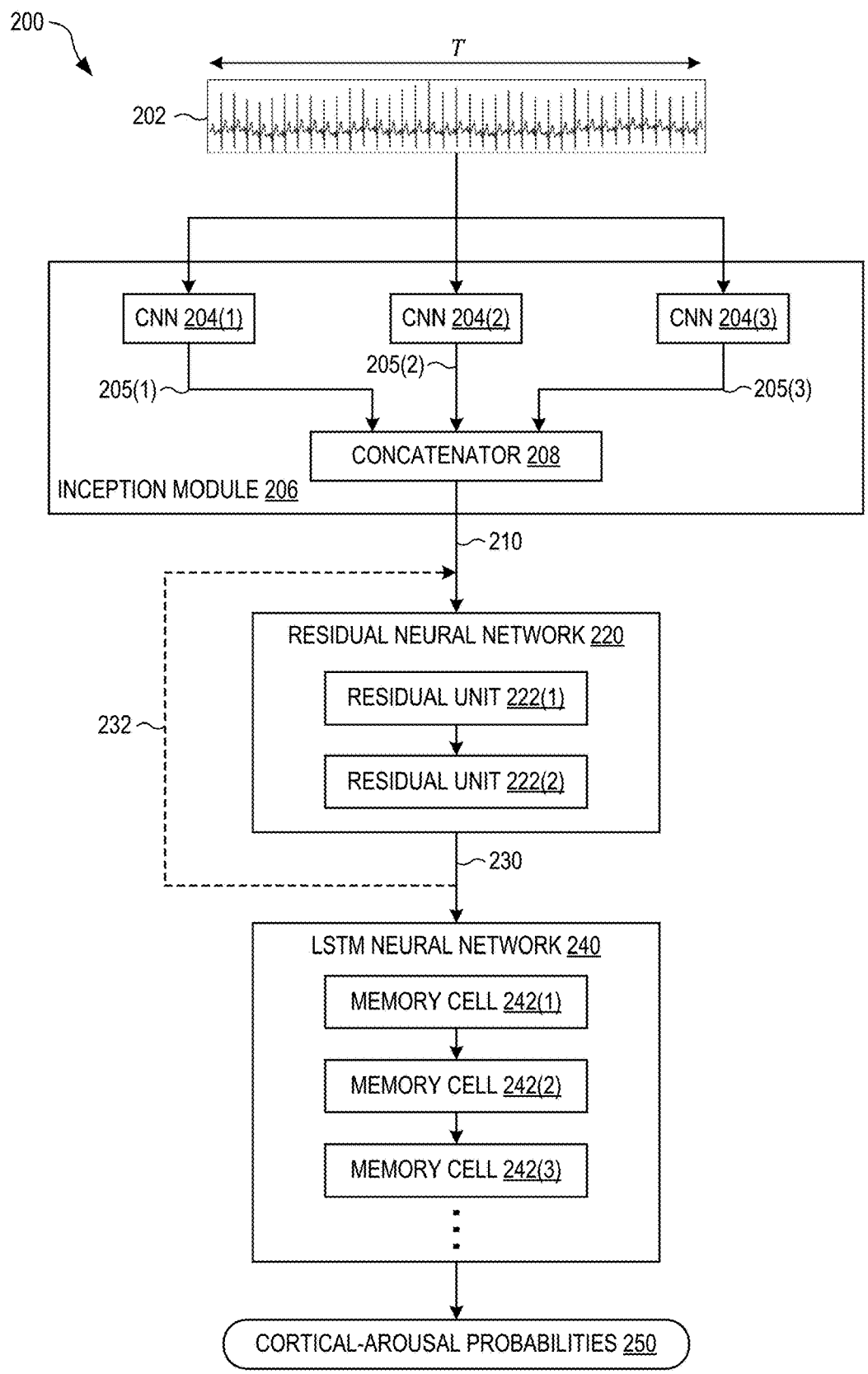
FIG. 2 shows a deep neural network that is pre-trained to process an ECG sequence into a sequence of cortical-arousal probabilities, in an embodiment.

FIG. 2 shows a deep neural network 200 that is pre-trained to process an ECG sequence 202 into a sequence of cortical-arousal probabilities 250. The deep neural network 200 includes an inception module 206 that extracts features from the ECG sequence 202. Although FIG. 2 shows the ECG sequence 202 with a duration T of 30 s, the ECG sequence 202 may have a duration T of several hours or more. The number of data points N in the ECG sequence 202 is $N=Tf_s$, or 921,600 data points per hour for $f_s=256$ Hz. Thus, the ECG sequence 202 may contain millions of data points, or more. The ECG sequence 202 may be stored in a computing device as a one-dimensional array of length N (e.g., the ECG monitor 300 of FIG. 3).

The inception module 206 contains a plurality of machine-learning or statistical models that process the ECG sequence 202 in parallel. Each machine-learning model applies one or more filters, or kernels, to the ECG sequence 202 to obtain one or more corresponding feature maps. Each filter has a different combination of size (i.e., the number of sequential values of the ECG sequence 202 to which the filter is applied) and weights (or kernel coefficients). The inception module 206 also includes a concatenator 208 that concatenates all of the feature maps from all of the machine-learning models to create a channel array 210.

In embodiments, the machine-learning models are artificial neural networks. For example, the machine-learning models may be convolutional neural networks (CNNs) 204, as shown in FIG. 2. Specifically, the inception module 206 includes a first CNN 204(1) that outputs feature maps via a first channel 205(1), a second CNN 204(2) that outputs additional feature maps via a second channel 205(2), and a third CNN 204(3) that outputs even more feature maps via a third channel 205(3). The inception module 206 may include more or fewer CNNs 204, and corresponding channels 205, than shown in FIG. 2 without departing from the scope hereof. The CNNs 204 convolve the ECG sequence 202 at different timescales. For example, the CNNs 204(1), 204(2), and 204(3) may have filter sizes of 11, 15, and 23 data points, respectively. For $f_s=256$ Hz, these filter sizes correspond to timescales of 43 ms, 59 ms, and 90 ms, respectively. However, the CNNs 204 may use any combination of filter sizes without departing from the scope hereof. Each CNN 204 may have a single layer or multiple layers. One or more of the CNNs 204 may include a pooling layer, such as a max pooling layer. Alternatively or additionally, a pooling layer may be used as one of the plurality of machine-learning models.

When the stride of a convolutional filter in FIG. 2 is set to one, the number of values in each feature map equals the number of data points N in the ECG sequence 202 (assuming the N data points are padded appropriately). Thus, each feature map may also be implemented as a one-dimensional array of length N. The concatenator 208 concatenates all of the feature maps from all of the CNNs 204 into a two-dimensional channel array 210 with N rows and F columns, where F is the total number of filters of all the CNNs 204. For example, each of the four CNNs 204 may have eight filters, wherein F=32. The stride of each filter may be alternatively set to a value greater than 1, wherein the number of rows N is reduced accordingly.

In other embodiments, the inception module 206 does not use CNNs. For example, the inception module 206 may apply a window function (e.g., a non-overlapped Hann taper function) to the ECG sequence 202 to create a spectrogram. The inception module 206 may output at least part of the spectrogram as the channel array 210. The inception module 206 may use another type of machine-learning model without departing from the scope hereof. In some embodiments, the inception module 206 uses more than one type of machine-learning model.

Inception modules were first disclosed by Christian Szegedy et al. in "Going deeper with convolutions" (arXiv: 1409.4842, 2014), which describes the well-known GoogLeNet submission to the 2014 ImageNet Large-Scale Visual Recognition Challenge (ILSVRC). This reference shows two versions of an inception module: a naive version and a version with dimension reduction. This latter version uses 1×1 convolutions to reduce the red, green, and blue channels of a color image to a single channel prior to applying 3×3 and 5×5 convolutions. This dimension reduction prevents the 3×3 and 5×5 convolutions from becoming prohibitively expensive. In the present embodiments, the ECG sequence 202 occupies only a single channel, and therefore 1×1 convolutions are not needed. Convolutions are also faster in the present embodiments because the ECG sequence 202 spans only one dimension (i.e., time) rather than two. For this reason, the inception module 206 in FIG. 2 appears more like the naive version shown in the reference. However, it should be understood that any inception-module-based architecture may be used for the inception module 206 without departing from the scope hereof.

The deep neural network 200 also includes a residual neural network 220 that both extracts features from the channel array 210 and downsamples the channel array 210 into a downsampled channel array 230. The residual neural network 220 contains a sequence of one or more residual units 222, of which only two are shown in FIG. 2. However, the residual neural network 220 may contain only one residual unit 222, or more than two residual units 222, without departing from the scope hereof.

Residual units were first disclosed by He et al. in "Deep Residual Learning for Image Recognition" (arXiv: 1512.03385v1, 2015), which describes Microsoft's well-known ResNet architecture for the 2015 ILSVRC. Additional details about residual units were subsequently disclosed by He et al. in "Identity Mappings in Deep Residual Networks" (arXiv:1603.05027v3, 2016). As described in these references, each residual unit 222 splits its input into two pathways (also see FIG. 10A). In the first pathway, the input data is processed with a neural network, such as a CNN. This first pathway is pre-activated, meaning that activation functions precede weight layers. The second pathway acts as a shortcut connection that bypasses the first pathway and maps the identity function between the input and output. Each residual unit also includes an adder that pointwise adds the outputs of the first and second pathways to create a single output. The above references by He et al. disclose various architectures for residual units that implement different types of pre-activation and shortcut connections. Any of these residual-unit architectures may be used for the residual units 222 in FIG. 2. An alternative type of residual-unit architecture may be used for the residual units 222 without departing from the scope hereof.

Figure 10A:
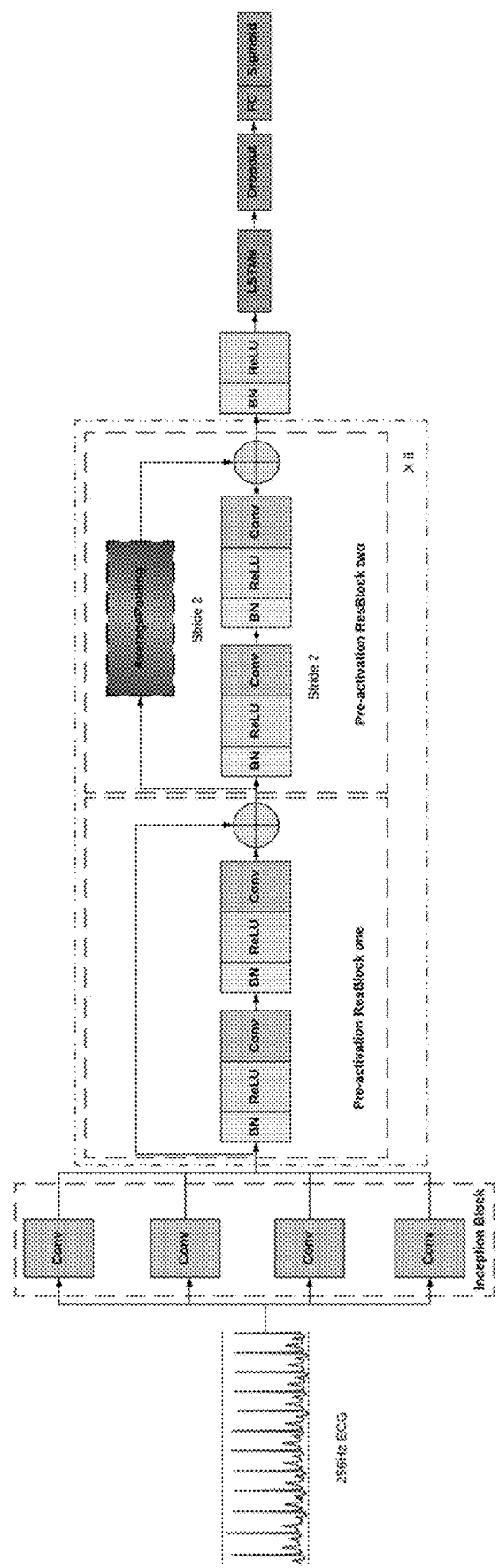
FIG. 10A shows the detailed architecture of the model. Here, "Conv" indicates a convolutional layer, "Concate" indicates the concatenation of four tensors, "BN" indicates batch normalization, "ReLU" indicates a rectified linear unit, and "FC" indicates a fully connected layer.

In some embodiments, a first residual unit 222(1) is a non-downsampling residual unit that uses a CNN with a stride of one and padding. In this case, the output of the first residual unit 222(1) has the same size as the input. The second residual unit 222(2) is a downsampling residual unit that uses a CNN with a downsampling stride greater than one. In this case, the output of the second residual unit 222(2) is smaller than its input by a factor of the downsampling stride. For example, when the downsampling stride is two, the output of the second residual unit 222(2) is one-half the size of its input. The downsampling stride may be used in both pathways of the second residual unit 222(2), e.g., in a CNN of the first pathway and pooling layer of the second pathway. The non-downsampling first residual unit 222(1) may be excluded such that the residual neural network 220 includes only the downsampling second residual unit 222 (2). FIG. 10A shows one example of these embodiments.

In some embodiments, the deep neural network 200 iterates over the residual neural network 220 to repeatedly downsample the channel array 210. As shown in FIG. 2, this may be implemented with a feedback path 232 that connects the output of the residual neural network 220 to its input. For example, when the downsampling stride is two and the deep neural network 200 iterates over the residual neural network 220 k times, the downsampled channel array 230 is smaller than the channel array 210 by a factor of $2^k$. Furthermore, the number of filters implemented in the CNN of the first pathway may be increased with each iteration.

The deep neural network 200 also includes a long short-term memory (LSTM) neural network 240 that calculates, based on the downsampled channel array 230, the sequence of cortical-arousal probabilities 250. The LSTM neural network 240 may use a sequence of LSTM memory cells 242, of which three are shown in FIG. 2, However, the LSTM neural network 240 may use only two memory cells 242, or more than two memory cells 242, without departing from the scope hereof. In any case, each memory cell 242 has an input cell state, an output cell state, an input hidden state, and an output hidden state. For each memory cell 242, the output hidden state is connected to the input hidden state, while the output cell state is connected to the input cell state of a next memory cell 242 of the sequence. The input cell state of the first memory cell 242(1) of the sequence receives the downsampled channel array 230 and the output cell state of the last memory cell 242 of the sequence is then processed into the sequence of cortical-arousal probabilities 250. Although not shown in FIG. 2, one or more of a nonlinear layer (e.g., sigmoid), dropout layer, and fully-connected layer may be used to process the output of the sequence of memory cells 242 into the sequence of cortical-arousal probabilities 250. Without departing from the scope hereof, each of the LSTM memory cells 242 may alternatively implement another type of memory cell used with recurrent neural networks, such as a gated recurrent unit.

Figure 3:
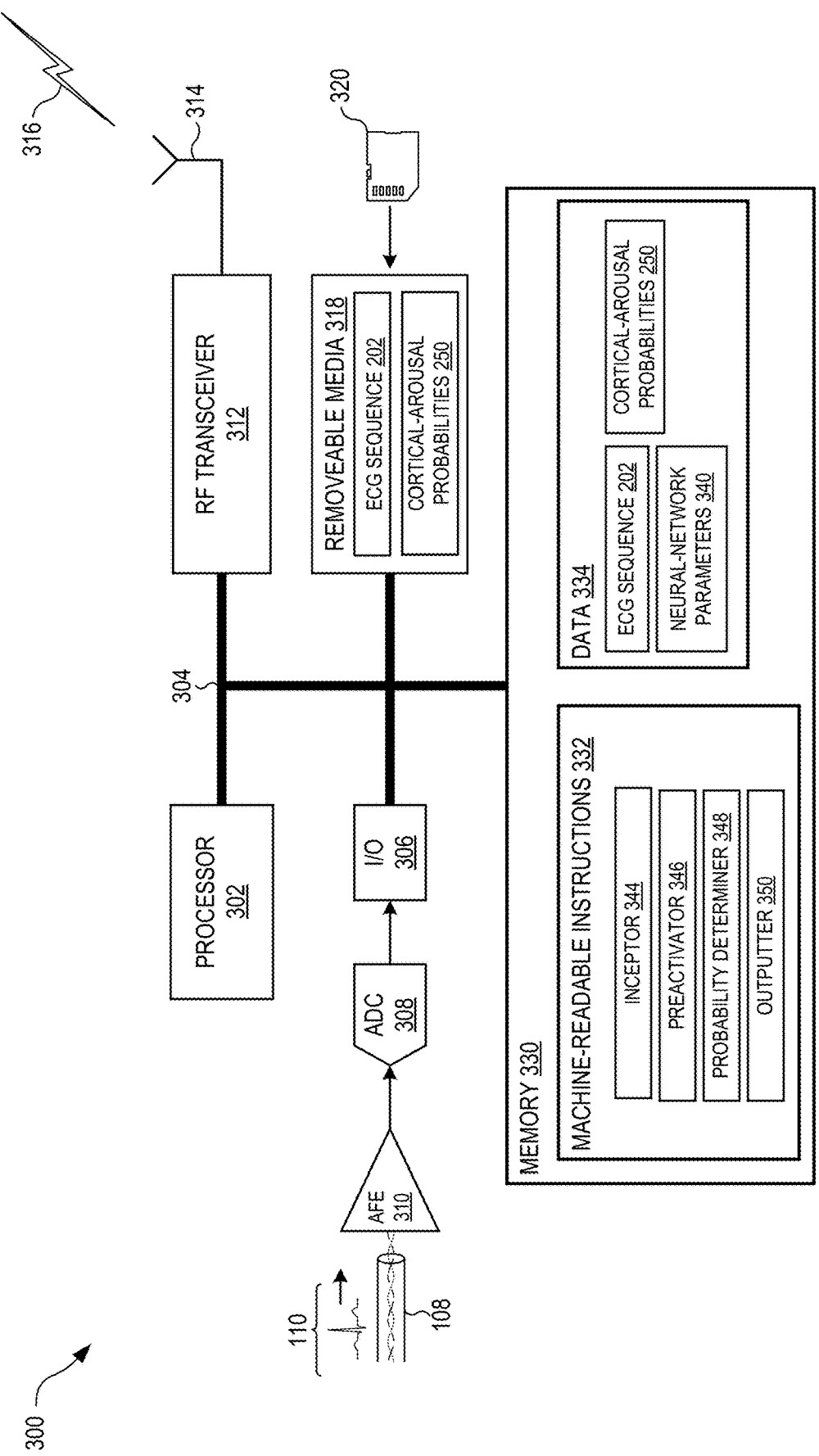
FIG. 3 is a functional diagram of an ECG monitor that processes the ECG signal of FIG. 1 with the deep neural network of FIG. 2 to identify one or more periods of cortical arousal, in an embodiment.

FIG. 3 is a functional diagram of an ECG monitor 300 that processes the ECG signal 110 with the deep neural network 200 to identify one or more periods of cortical arousal that occur while the person 102 sleeps. The ECG monitor 300 is one example of the ECG monitor 100 of FIG. 1. The ECG monitor 300 is a computing device having a processor 302 and memory 330 that communicate with each other over a system bus 304. The memory 330 stores machine-readable instructions 332 that, when executed by the processor 302, control the ECG monitor 300 to implement the functionality and methods described herein. The memory 330 also stores data 334 used by the processor 302 when executing the machine-readable instructions 332. In the example of FIG. 3, the data 334 stores the ECG sequence 202, neural-network parameters 340 for the deep neural network 200 of FIG. 2 (e.g., weights and biases), and the sequence of cortical-arousal probabilities 250. Each value of the ECG sequence 202 has a corresponding time that may be implicit based on the location of the value in the ECG sequence 202, or explicitly stored with the value as a time stamp. Each of the cortical-arousal probabilities 250 indicates a probability of cortical arousal at a certain time of the ECG sequence 202. As described previously, the ECG sequence 202 is downsampled, and therefore a time spacing $\Delta t_p$ between sequential cortical-arousal probabilities 250 is larger than the time spacing $\Delta t_s$ of the ECG sequence 202. For example, $\Delta t_p$ may be 1 s, while $\Delta t_s$ may be 1/(256 Hz)=3.9 ms. Other values of $\Delta t_p$ and $\Delta t_s$ may be used without departing from the scope hereof.

In the example of FIG. 3, the machine-readable instructions 332 store an inceptor 344, a preactivator 346, and a probability determiner 348 that together implement the deep neural network 200. Specifically, the inceptor 344 implements the inception module 206 of FIG. 2, the preactivator 346 implements the residual neural network 220, and the probability determiner 348 implements the LSTM neural network 240. The machine-readable instructions 332 also store an outputter 350 that outputs the sequence of cortical-arousal probabilities 250. The outputter 350 may also output the ECG sequence 202. The memory 330 may store additional data 334 and machine-readable instructions 332 than shown in FIG. 3 without departing from the scope hereof.

The processor 302 may be any type of circuit or integrated circuit capable of performing logic, control, and input/output operations. For example, the processor 302 may include one or more of: a microprocessor with one or more central processing unit (CPU) cores, a graphics processing unit (GPU), a digital signal processor (DSP), a field-programmable gate array (FPGA), a system-on-chip (SoC), a microcontroller unit (MCU), and an application-specific integrated circuit (ASIC). The processor 302 may include a memory controller, bus controller, and other components that manage data flow between the processor 302, the memory 330, and other components communicably coupled to the system bus 304.

In some embodiments, the ECG monitor 300 includes an analog front end (AFE) 310 that amplifies and/or filters the ECG signal 110, an analog-to-digital converter (ADC) 308 that digitizes the amplified/filtered ECG signal 110 into a sequence of digital values, and an I/O block 306 that outputs the sequence of digital values from the ADC 308 for storage in the memory 330. In other embodiments, the ECG monitor 300 receives the ECG sequence 202 from a separate ECG monitoring device that processes and digitizes the ECG signal 110. For example, the ECG monitor 300 may receive the ECG sequence 202 via a wired connection (e.g., Ethernet, USB) or a wireless connection (e.g., Bluetooth, Wi-Fi).

In some embodiments, the ECG monitor 300 includes a removeable media block 318 that may be used to store the sequence of cortical-arousal probabilities 250 on a removable memory 320 (e.g., a SD card). The ECG sequence 202 may also be stored on the removable memory 320, as shown in FIG. 3. These embodiments allow an entire night's worth of data to be easily transferred to a doctor or clinician for subsequent review and interpretation.

In some embodiments, the ECG monitor 300 includes a radio-frequency (RF) transceiver 312 that may be used to wirelessly receive the ECG sequence 202, wirelessly transmit the sequence of cortical-arousal probabilities 250, or both. The RF transceiver 312 may be used with a wireless network, such as Bluetooth or Wi-Fi. For example, the ECG monitor 300 may use the RF transceiver 312 to wirelessly transmit the ECG sequence 202 and sequence of cortical-arousal probabilities 250 to a local computer (e.g., desktop or laptop), tablet, or mobile device that stores the ECG sequence 202 and cortical-arousal probabilities 250 until it is ready to transfer to a health-care provider for subsequent review and interpretation. Although not shown in FIG. 3, the ECG monitor 300 may similarly communicate with the local computer, tablet, or mobile device using a wired connection, such as USB, FireWire, or Ethernet.

In some embodiments, the ECG monitor 300 uses the RF transceiver 312 to connect to the Internet, in which case the ECG monitor 300 may wirelessly communicate the ECG sequence 202 and cortical-arousal probabilities 250 to a remote computer system (e.g., in the cloud). For example, the RF transceiver 312 may use 4G or 5G cellular communications to access the remote computer system. A health-care provider can then subsequently download the ECG sequence 202 and cortical-arousal probabilities 250 from the remote computer system for subsequent review and interpretation. The ECG monitor 300 may similarly communicate with the remote computer using a wired network connection, such as Ethernet.

In some embodiments, the ECG monitor 300 includes a screen for visually displaying the ECG sequence 202 and/or the sequence of cortical-arousal probabilities 250. The display may also be used to indicate, in real-time, when a most-recent value of the sequence of cortical-arousal probabilities 250 is above a threshold, indicating that the person 102 is currently experiencing cortical arousal. Some of these embodiments may be similar to patient monitors used in hospitals, except configured to display the sequence of cortical-arousal probabilities 250. In some of these embodiments, the ECG monitor 300 is a local computer (e.g., desktop or laptop), tablet, or mobile device that has received the ECG sequence 202 and the sequence cortical-arousal probabilities 250 and displays one or both of the ECG sequence 202 and the sequence of cortical-arousal probabilities 250. In other embodiments, the ECG monitor 300 is a local computer (e.g., desktop or laptop), tablet, or mobile device that receives only the ECG sequence 202 and processes the ECG sequence 202 to obtain the sequence of cortical-arousal probabilities 250.

Demonstration

As a demonstration of the present embodiments, we developed and evaluated an end-to-end deep learning approach to detect cortical arousals during sleep using a one-night single lead ECG signal. Our end-to-end deep learning-based cortical arousal detection (DeepCAD) model combines both CNN and recurrent neural networks (RNN). This DeepCAD model, which is one embodiment of the deep neural network 200 of FIG. 2, has the ability to extract spatiotemporal features from raw 256-Hz ECG data to detect arousals with one second resolution. We developed and evaluated the DeepCAD model using the Multi-Ethnic Study of Atherosclerosis (MESA), a large manually-scored dataset of home-acquired polysomnography (PSG). To evaluate the generalizability of the algorithm, we also applied the DeepCAD model to the Sleep Heart Health Study (SHHS), which is another dataset of home-acquired PSG.

Source and Evaluation Databases—We used the MESA database to develop and test the DeepCAD model. The MESA is a multi-center longitudinal cohort study sponsored by the National Heart Lung and Blood Institute (NHLBI). Its overall goals are to investigate characteristics of subclinical cardiovascular disease and their progression to overt disease. Between 2010 and 2012, 2,237 of the original 6,814 participants were enrolled in a sleep exam, which included full overnight unattended PSG, seven-day wrist-worn actigraphy, and a sleep questionnaire.

The SHHS database was used to evaluate the generalizability of the DeepCAD algorithm. The SHHS was a multi-center longitudinal cohort study sponsored by the NHLBI to determine whether OSA was a risk factor for the development of cardiovascular disease. During the second exam cycle of the SHHS, between 2001 and 2003, 3,295 participants had full overnight PSG performed in the home. Both the MESA and SHHS databases are publicly accessible at the National Sleep Research Resource (NSRR).

Unattended Polysomnogram—In the MESA sleep exam, all participants underwent home PSG. The PSG records were recorded using the Compumedics Somte System (Compumedics Ltd., Abbotsford, Australia) that included a single-lead ECG, three EEG derivations, two EOG derivations, chin EMG, thoracic and abdominal respiratory inductance plethysmography, airflow, leg movements, putative snoring, and finger-pulse oximetry. The sampling frequencies of ECG, EEGs, EMG, and EOGs were 256 Hz.

In the SHHS sleep exam, home PSG was recorded using the Compumedics P Series System (Compumedics Ltd., Abbotsford, Australia) that included a single-lead ECG, two EEG derivations, two EOG derivations, chin EMG, thoracic, abdominal respiratory inductance plethysmography, airflow, and finger pulse oximetry. In contrast to the MESA, the sampling frequencies of the ECG and EEG for the SHHS sleep exam were 250 and 125 Hz, respectively.

EEG Arousal Scoring—For both the MESA and SHHS sleep exams, certificated scorers manually scored cortical arousal events on Compumedics software based on the AASM criteria. Cortical arousals were scored separately from sleep stages. The AASM defines cortical arousal as an abrupt shift in EEG frequency, which may include alpha and/or theta waves and/or delta waves and/or frequencies greater than 16 Hz lasting at least three seconds and starting after at least ten continuous seconds of sleep. In rapid-eye movement (REM) sleep, an increase in the EMG signal is also required.

Development and Test Datasets—The publicly accessible MESA database included 2,056 raw PSG records from 2,056 unique participants. We excluded PSG records which had less than 50% ECG signal available during the time spent asleep. We also excluded records that were only scored sleep/wake, were labeled as having unreliable arousal scoring, or did not have cortical arousal annotations. Thus, there were 1,547 records available for analysis. We randomly separated the 1,547 records into a training set with 1,236 records and a test set with 311 records. Table 1 below describes the characteristics of the training set and the test set. The training set was further randomly divided into a training subset with 1,112 records and a validation subset with 124 records for development. We labeled each second of data as arousal "present/not present" based on the NSRR cortical arousal annotation. The binary labels were used as ground truth. To minimize the influence of unreadable signals, we extracted the segment starting thirty seconds before the first positive ground truth arousal label of the one-night record to thirty seconds after the last positive ground truth arousal label of the one-night record for this study (see Appendix A below).

TABLE 1

Characteristics of the data sets. The number of arousals and arousal duration were based on the manually scored annotations.

| | MESA | | SHHS | |
|---|---|---|---|---|
| | Training set (n = 1236) | Test set (n = 311) | Training set (n = 1176) | Test set (n = 785) |
| % Female | 51.62 | 57.56 | 55.5 | 54.6 |
| | mean ± SD | mean ± SD | mean ± SD | mean ± SD |
| Age | 69.02 ± 8.94 | 69.06 ± 8.83 | 66.92 ± 10.09 | 67.53 ± 10.20 |
| AHI | 19.89 ± 17.97 | 18.34 ± 15.82 | 13.81 ± 13.39 | 14.80 ± 15.29 |
| Total record time (min) | 636.94 ± 86.15 | 634.44 ± 93.52 | 596.50 ± 65.93 | 601.48 ± 64.33 |
| Total sleep time (min) | 361.14 ± 81.06 | 364.00 ± 82.71 | 377.13 ± 66.01 | 377.42 ± 68.40 |
| Number of arousals | 158.76 ± 80.99 | 158.09 ± 81.78 | 131.18 ± 67.29 | 133.84 ± 63.16 |
| Total arousal duration (sec) | 1679.64 ± 883.81 | 1671.89 ± 928.80 | 1328.35 ± 649.49 | 1360.37 ± 637.43 |

AHI: Apnea-Hypopnea Index ≥ 4%: number of all apneas and hypopneas with ≥ 4% oxygen desaturation or arousal per hour of sleep.

The publicly accessible second examination SHHS database included 2,651 raw PSG records from 2,651 unique subjects. After excluding the scoring unreliable PSG records, we split the dataset (n=1961 records) into a training set (n=1058), a validation set (n=118), and a test set (n=785). The identification of the presence of arousals was performed identically to the procedure used for the MESA datasets.

Preprocessing ECG Data—We intended to minimize the complexity of preprocessing and use less expert knowledge about the relationships between ECG signals and cortical arousals in development. Therefore, in the preprocessing stage, we only standardized each one-night ECG signal using the Scikit-learn's robust scaler, which removed the median and divided each sample by the interquartile range.

Figure 4:
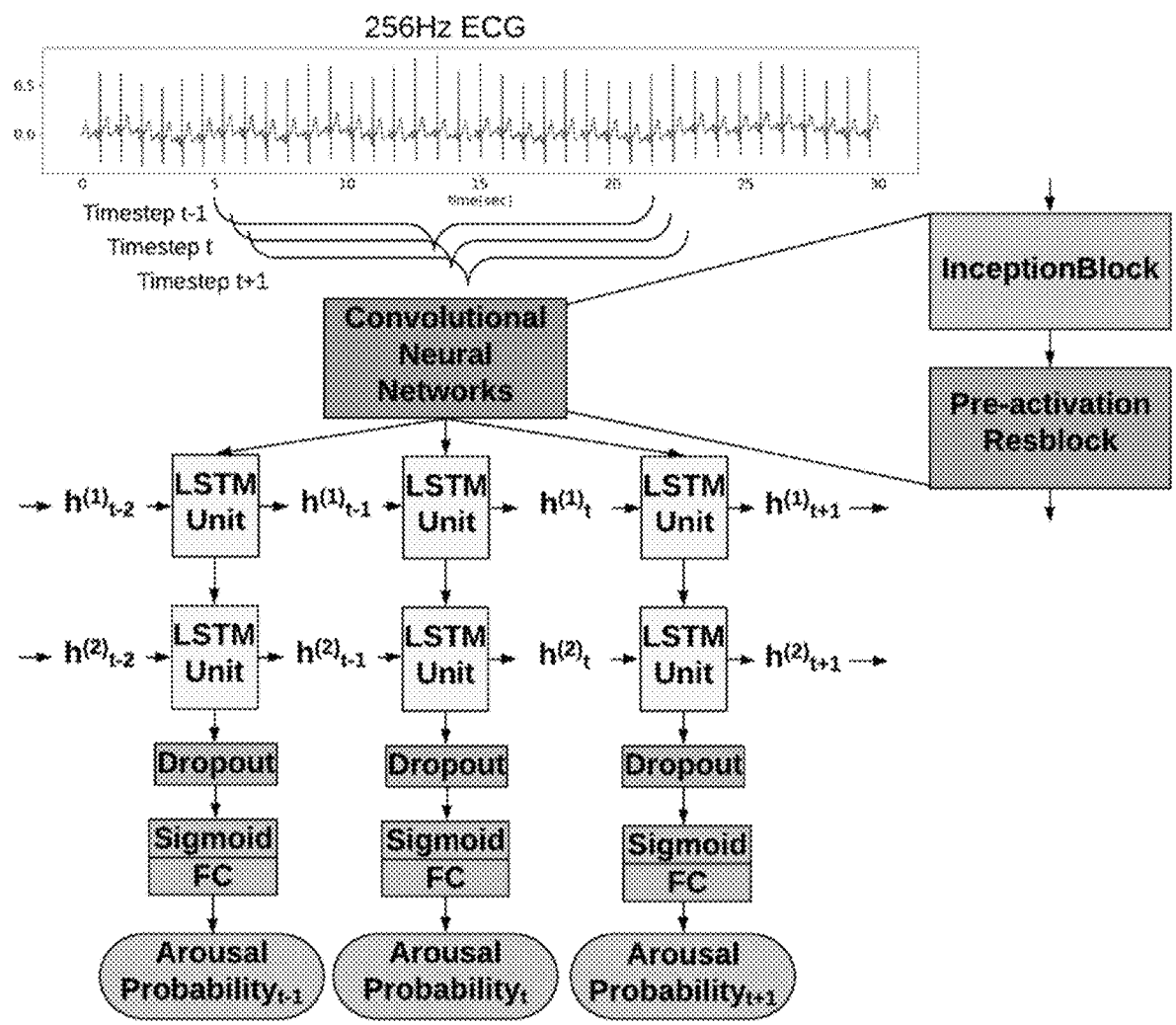
FIG. 4 shows a model architecture, in an embodiment. The input is a sequence of 256 Hz ECG signal. The convolutional neural networks (CNNs) include two main blocks, inception block and pre-activation residual block (Resblock). The CNNs are applied to extract spatial features from the ECG signal by filters and moving windows. The extracted features are passed into long short-term memory (LSTMs) layer, where t indicates timestep and h indicates the hidden cells which pass the information from one timestep to the next timestep. The output of the model is a sequence of probabilities of presence arousal.

Models Development—We developed an end-to-end learning model to detect arousals. It used raw ECG signal as input; the model produced a new output (arousal probability) every one second. The architecture of the proposed Deep-CAD model is shown in FIG. 4 and the hyper-parameters are listed in Appendix B below. The DeepCAD model had 33 convolutional layers, two long short-term memory (LSTM) layers, and a fully connected layer. The convolutional layers are effective feature extractors with filters and moving windows which are able to learn relevant features from the ECG data. We used batch normalization and a rectified linear unit activation function after each convolutional layer. To increase the flexibility of the model and ability to extract information on multiple time scales, we used multiple filters with various filter sizes as the first CNN layer to extract information from the raw ECG signal. The first layer structure was termed the inception block. We also used pre-activation residual blocks (ResBlocks) to extract spatial features from the raw 256-Hz ECG signal, and to down-sample the input to 1 Hz before it was passed into the LSTM layers. The concept of ResBlocks is known in the prior art for solving the training problem of deep neural networks and improving generalization. The LSTM is a specialized type of RNN, including memory cells, that can learn long-range dependencies. An unfolded LSTM layer includes multiple weight-shared LSTM units. The number of units is equal to the number of seconds of the 1-Hz input (see FIG. 4). The two inputs of each LSTM unit of the first layer are the outputs of the previous LSTM unit and the ECG features which were extracted by CNN. We used a dropout layer atop the highest LSTM layer to reduce overfitting. It was followed by a fully connected layer with a sigmoid activation function for producing probability of arousal. Appendix B below includes a detailed description of the model architecture. For evaluating the importance of individual components, multiple alternative architectures were also developed with the training set, including a spectrogram and LSTMs model, an inception block and LSTMs model, a two-layer LSTM model, a ResBlocks and LSTMs model, and an inception block and ResBlocks model (see Appendix C). Model development was performed using PyTorch.

We used cross-entropy as the loss function:

$$\mathcal{L} = -\frac{1}{N}\sum_{i=1}^{N} y_i \log \hat{y}_i + (1-y_i)\log(1-y_i),$$

where $y_i \in \{0,1\}$ is the ground truth label, $\hat{y}_i \in [0,1]$ is the arousal probability, i is the sample index, and N is the total number of samples in one batch. We trained the models using truncated backpropagation-through-time with a depth of 90 and an Adam algorithm ($\beta_1$=0.9, $\beta_2$=0.999) with L2 weight decay ($\lambda=10^{-5}$) on the training set. We set a mini-batch size of 30 and initialized a learning rate to $10^{-4}$. In each epoch, we used the validation set to evaluate the performance of the model and reduced the learning rate by a factor of 10 when the performance stopped improving for four consecutive epochs. When the performance of the model on the validation dataset stopped improving within the error, we stopped the training process.

Because the model development included a number of hyper-parameters, we used a random search method with manual tuning to set their values. Generally, we set a search space and searched the learning rate, number of layers, the size and number of filters per layer, minibatch size, pooling method, etc. Then, we selected the model with highest gross area under the precision-recall curve (AUPRC) as the best model for our final DeepCAD model. This model had an AUPRC of 0.65 on the validation set. We also selected a decision threshold of 0.4 to classify each output as arousal "present/not present" based on the precision-recall curve of the DeepCAD model on the validation set.

Algorithm Evaluation—We evaluated the models on a holdout test set (n=311). We performed three types of evaluation: gross sequence level evaluation, event level evaluation, and record-wise evaluation. The gross sequence level AUPRC and area under receiver operating curve (AUROC) were calculated for the entire test set which consisted of the concatenated output probability sequence of each PSG record together as one sequence. Then, we compared the sequence against the ground truth labels for computing gross sequence level metrics. For event level evaluation, we used the selected decision threshold to classify each second to presence/no presence of an arousal. A set of continuous positive labels was considered as one arousal event. We recognized that the changes in the ECG signal may not have occurred simultaneously with changes in the EEG during a cortical arousal. Therefore, if the ground truth arousal and predicted arousal had overlap, we considered the predicted arousal as true positive. We also performed a record-wise evaluation in which we computed the AUPRC and AUROC for each PSG record. In addition, we correlated the number of detected arousal events with the number of ground truth arousal events for each PSG record. To determine whether all components of the DeepCAD model were essential to its optimum performance, we also performed a series of ablation experiments (see Table 3) where various components were omitted, and the respective AUPRC and AUROC were recalculated.

TABLE 2

Montage and Sampling Rate Comparison

| MESA | | | SHHS | | |
|---|---|---|---|---|---|
| Channel and Channel Derivation | Sampling Frequency (Hz) | Hardware Filters (Hz) | Channel and Channel Derivation | Sampling Frequency (Hz) | Hardware Filters (Hz) |
| ECG | 256 | — | ECG | 250 | High Pass 0.15 |
| EEG (Fz/Cz) | 256 | Low pass 100 | EEG (C3/A2) | 125 | High Pass 0.15 |
| EEG (Cz/Oz) | 256 | Low pass 100 | EEG (C4/A1) | 125 | High Pass 0.15 |
| EEG (C4/M1) | 256 | Low pass 100 | | | |

To assess the generalizability of the algorithm, we applied the DeepCAD model on a subset of Sleep Heart Health Study 2 (SHHS) data which was acquired by home PSG using different hardware filters and sampling rate (see Tables 1 and 2). Because the ECG sampling frequency of the SHHS data was 250 Hz, we used the NumPy one-dimensional interpolation method to resample the ECG signal to 256 Hz before applying the robust scaler. As shown in Table 4, we conducted four experiments for evaluating the algorithm on the SHHS data. In all experiments, we did not change any hyper-parameters of the DeepCAD model. In the first experiment, we directly applied the pretrained DeepCAD model (pretrained on MESA training set) to the SHHS test set (n=785). In the second experiment, we trained a random initialized DeepCAD model on the SHHS training set (n=1058) and tested it on the SHHS test set (n=785). In the third experiment, we used the DeepCAD model (pretrained on the MESA training set) and performed additional training on a small subset of the SHHS training set (n=105) before applying it to the SHHS test set (n=785). In the fourth experiment, we used the DeepCAD model (pretrained on the MESA training set) and performed additional training on the full SHHS training set (n=1058) before applying it to the SHHS test set (n=785).

TABLE 3

Performance of DeepCAD and alternative models

| Models | AUPRC | AUROC |
|---|---|---|
| Deep CAD (InceptionBlock + ResBlocks + LSTMs) | 0.62 | 0.93 |
| ResBlocks + LSTMs | 0.61 | 0.92 |
| InceptionBlock + LSTMs | 0.48 | 0.86 |
| InceptionBlock + ResBlocks | 0.46 | 0.87 |
| LSTMs | 0.39 | 0.82 |
| Spectorgram + LSTMs | 0.37 | 0.81 |

TABLE 4

Generalizability of the algorithm

Experiments

| Training set | Test set | Pretrained on MESA | AUPRC | AUROC |
|---|---|---|---|---|
| Pretrained on MESA | SHHS (n = 785) | — | 0.39 | 0.86 |
| SHHS (n = 1058) | SHHS (n = 785) | No | 0.54 | 0.91 |
| SHHS (n = 105) | SHHS (n = 785) | Yes | 0.52 | 0.91 |
| SHHS (n = 1058) | SHHS (n = 785) | Yes | 0.54 | 0.92 |

Statistical Analysis—Arousal detection has a high-class imbalance problem as the arousal events are relatively rare during the sleep period. Therefore, we used the AUPRC as a metric to evaluate performance. The precision-recall curve is a curve of precision versus recall/sensitivity with variance probability thresholds. The AUPRC is more informative of performance of the model because it only evaluates the performance on true positives. In this study, we used Scikit-learn's average precision method to compute the AUPRC. We also report the AUROC. The receiver operating curve is a curve of true positive rate (sensitivity) versus false positive rate (1−specificity) with variance probability thresholds. In the record-wise evaluation, we report the Pearson correlation between the number of detected arousal events and the number of ground truth arousal events. We also compared the difference between the two methods by a Bland-Altman plot. Analyses were performed using Python package Scikit-learn v0.20.1 and Scipy v1.3.0.

Figure 5A:
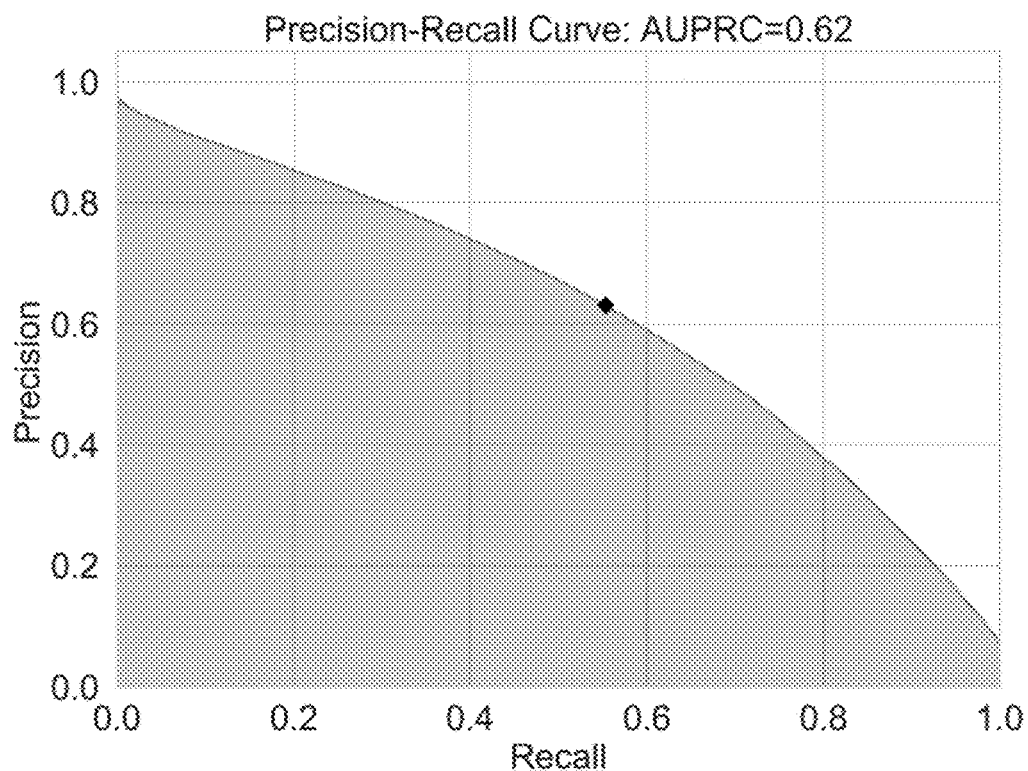
FIG. 5A shows a precision-recall curve and receiver operating characteristic curve. The diamonds correspond to the selected decision threshold of 0.40. The area under precision-recall curve (AUPRC) is 0.62.
Figure 5B:
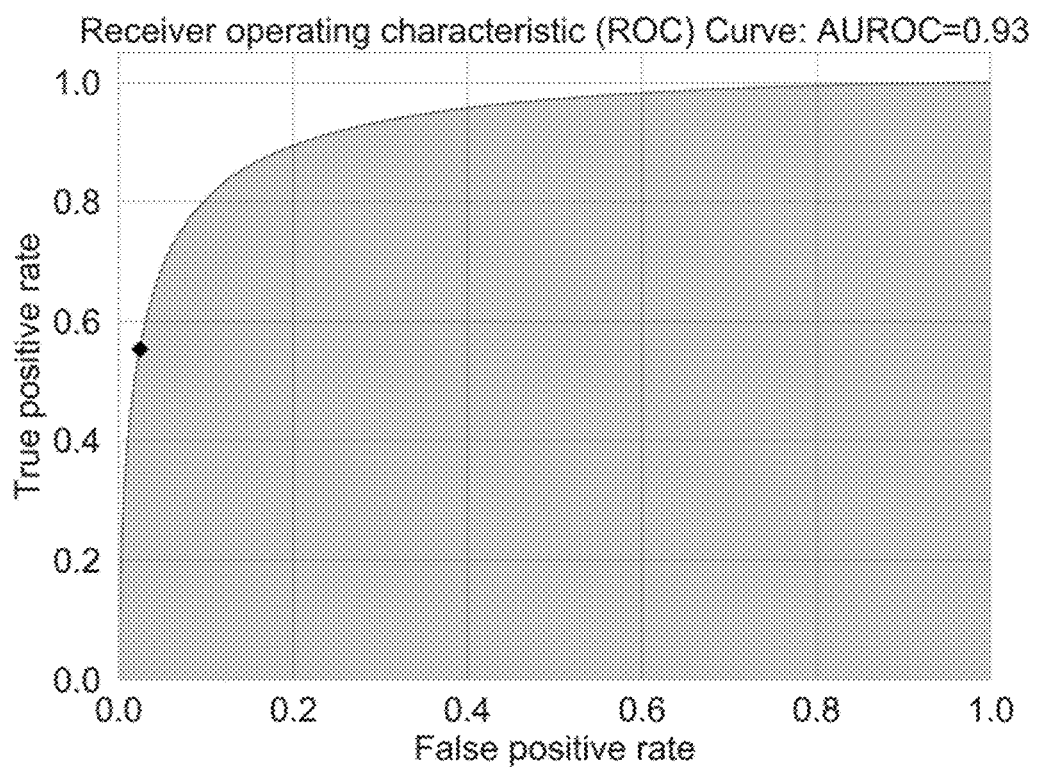
FIG. 5B shows a receiver operating characteristic curve. The diamonds correspond to the selected decision threshold of 0.40. The area under receiver operating characteristic curve (AUROC) is 0.93.
Figure 13:
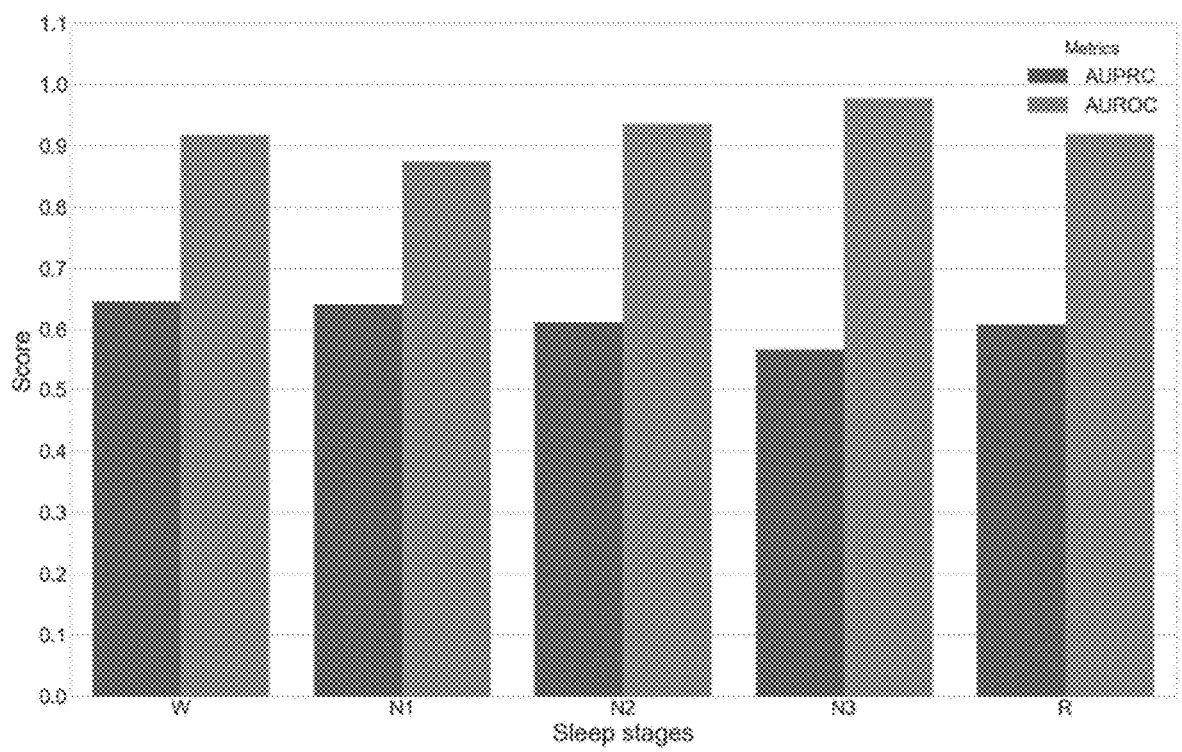
FIG. 13 illustrates performance in different sleep stages.
Figure 14:
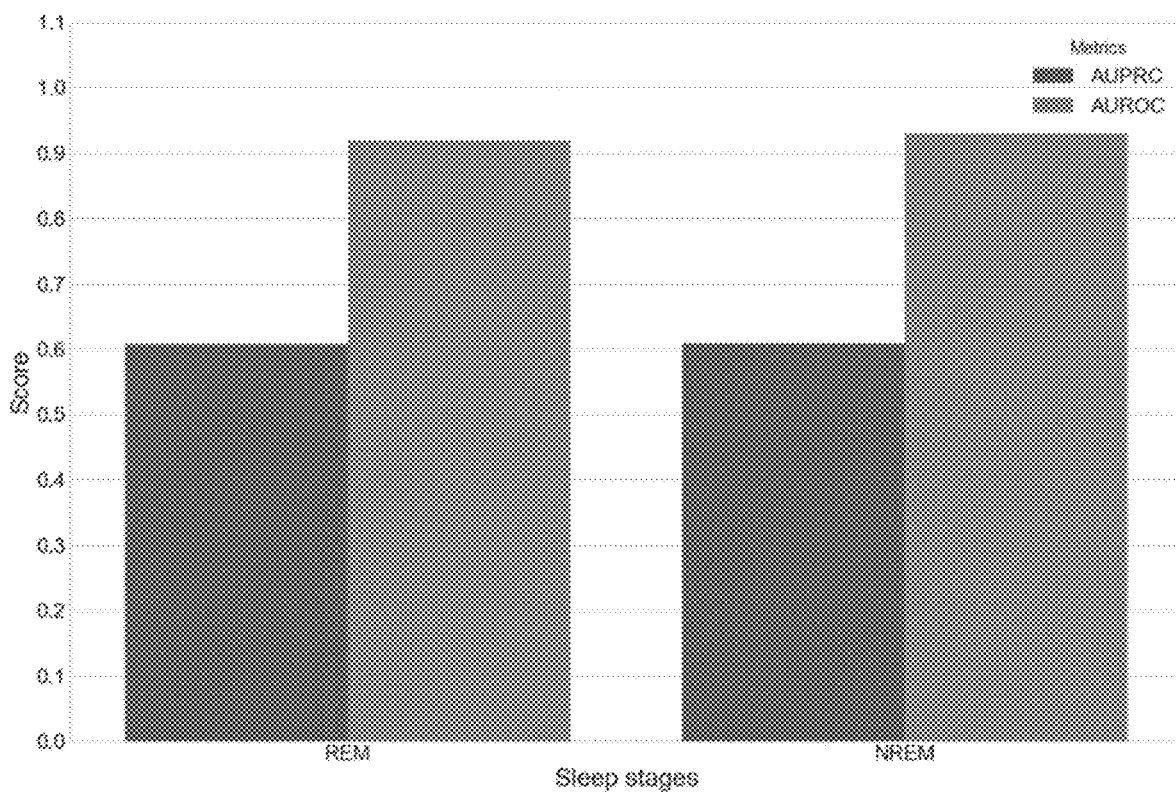
FIG. 14 illustrates performance in REM and NREM stages.

Results—The DeepCAD model with the AUPRC score of 0.65 on the validation set and the five alternative models were evaluated on the test set (n=311) for measuring the performance of the models. We report gross AUPRC and gross AUROC scores of the DeepCAD model and five alternative models in Table 3. The precision-recall curve and receiver operating characteristic curve of the DeepCAD model are shown in FIGS. 5A and 5B, respectively. Compared with the other five alternative models, the DeepCAD model had consistently better AUPRC and AUROC scores. The DeepCAD model also demonstrated similar performance during different sleep stages (see FIGS. 13 and 14).

Figure 6:
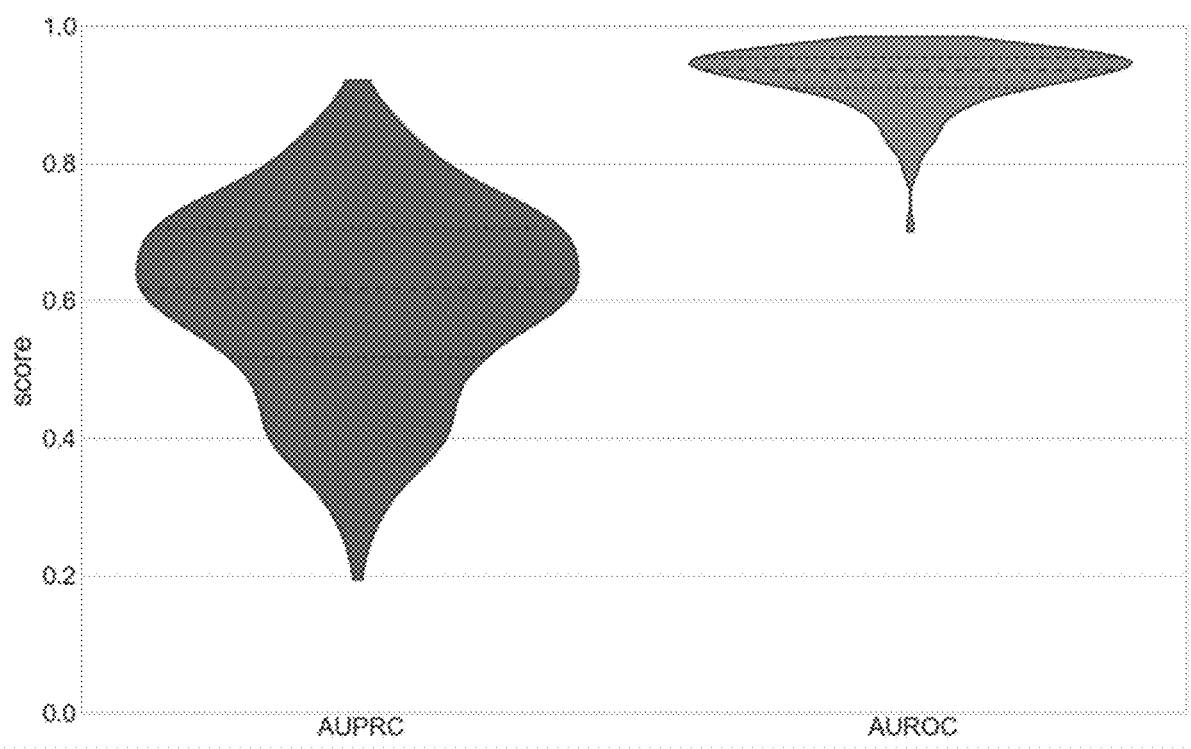
FIG. 6 shows the record-wise area under precision-recall curve (AUPRC) and area under receiver operating characteristic curve (AUROC). The violin plots represent the record-wise AUPRC and AUROC. The lines in the box correspond to the $25^{th}$, $50^{th}$, and $75^{th}$ percentiles. The shape shows the distributions of record-wise AUPRC and AUROC.
Figure 7A:
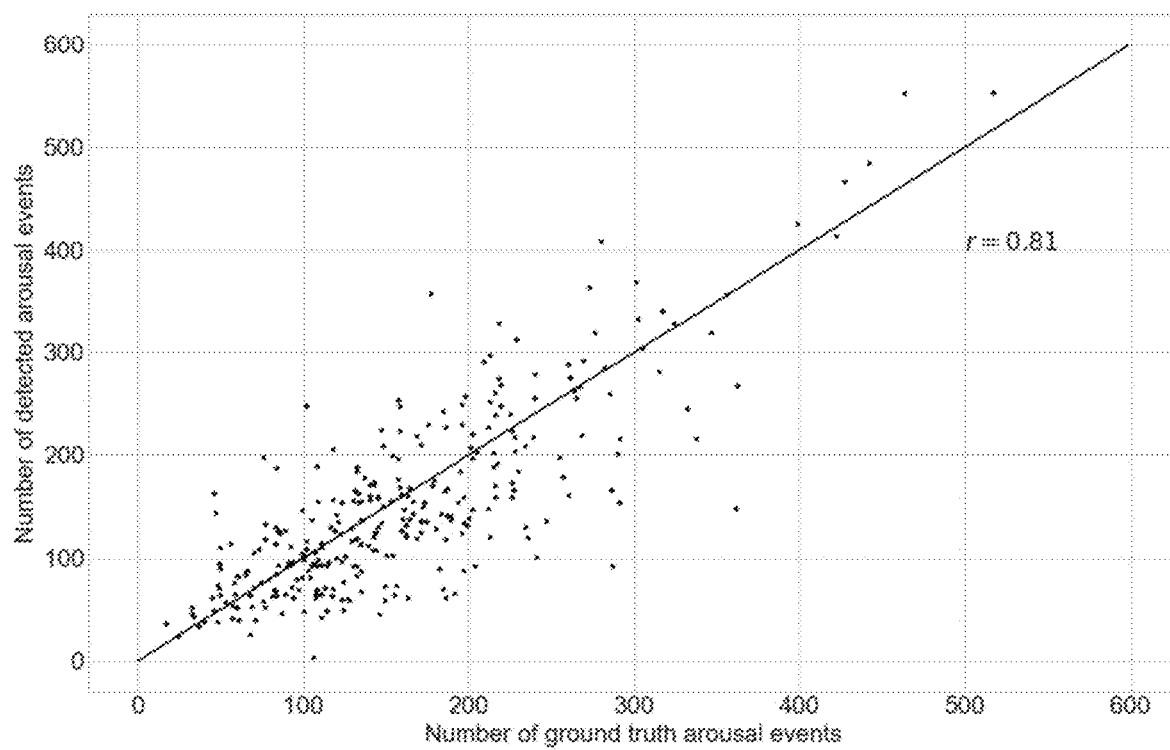
FIG. 7A is correlation plot between detected arousal events and ground truth arousal events.
Figure 7B:
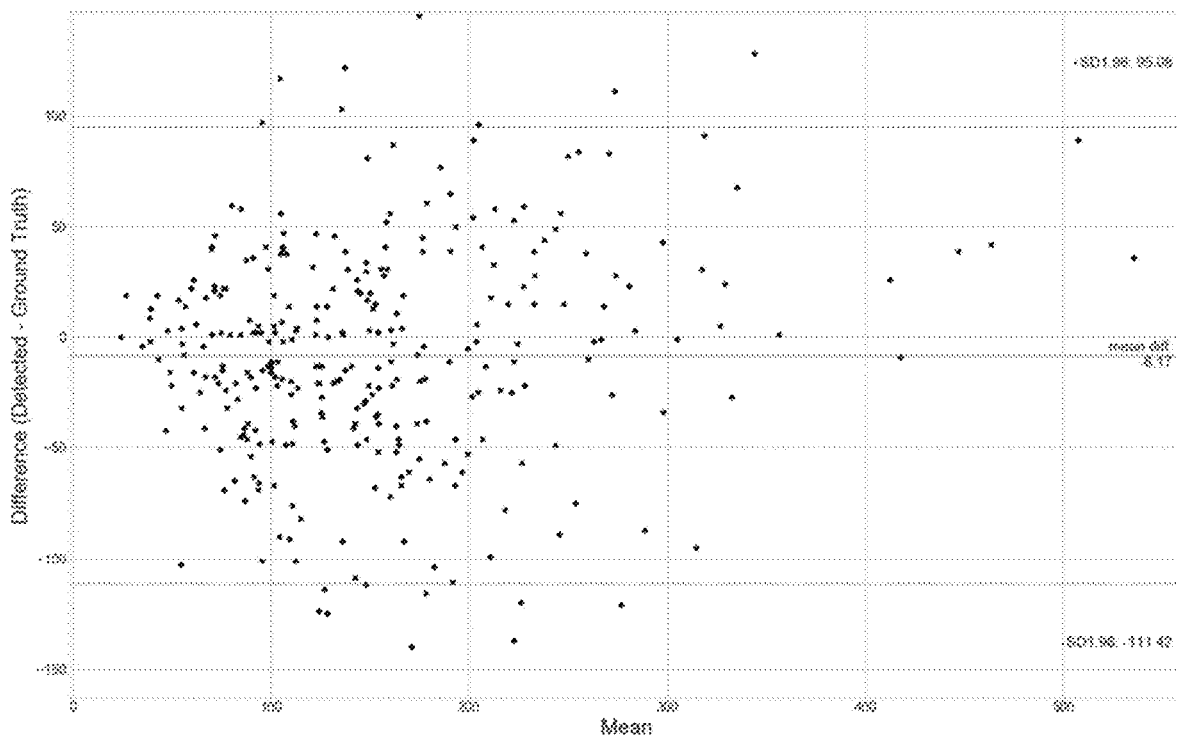
FIG. 7B is a Bland-Altman plot that accompanies the correlation plot of FIG. 7A.

In the event level evaluation, with the selected decision threshold of 0.4, the DeepCAD model had a 0.69 precision and 0.65 sensitivity on the test set. FIG. 6 shows the record-wise AUPRC and AUROC. Although the AUPRC scores varied widely across test records (Min: 0.19, Max: 0.92), the distribution representing the AUPRC scores is concentrated in the center. Additionally, FIG. 6 shows that over 80% of the records had AUROC scores higher than 0.9. FIG. 7A is a scatterplot of the number of detected arousal events versus the number of ground truth arousal events. The Pearson correlation between number of detected arousal events and the number of ground truth arousal events was 0.81 (p<0.0001). FIG. 7B is Bland-Altman plot that compares the difference between the automatic detection method and the ground truth. With the selected decision threshold of 0.4, the automatic detection method slightly underestimated total number of arousal events (mean difference=−8.17). The difference slightly widens as the average of number arousal events increases.

Table 4 shows the gross AUPRC and AUROC scores of the four experiments for evaluating generalizability. Although the two models trained on the full SHHS dataset (n=1058) exhibited the same AUPRC score of 0.54, the training time of the pretrained model is only one sixth of the model without pretraining. Additionally, the pretrained model that was trained on the full SHHS training set (n=1058) exhibited the highest AUROC score of 0.92. The pretrained model that was additionally trained on a small SHHS training set (n=105) had the closest performance with the two models that were trained on full SHHS training set (n=1058). The record-wise performances of four evaluation experiments are shown in Appendix D; these results show the same rankings as gross sequence level evaluation.

Figure 8A:
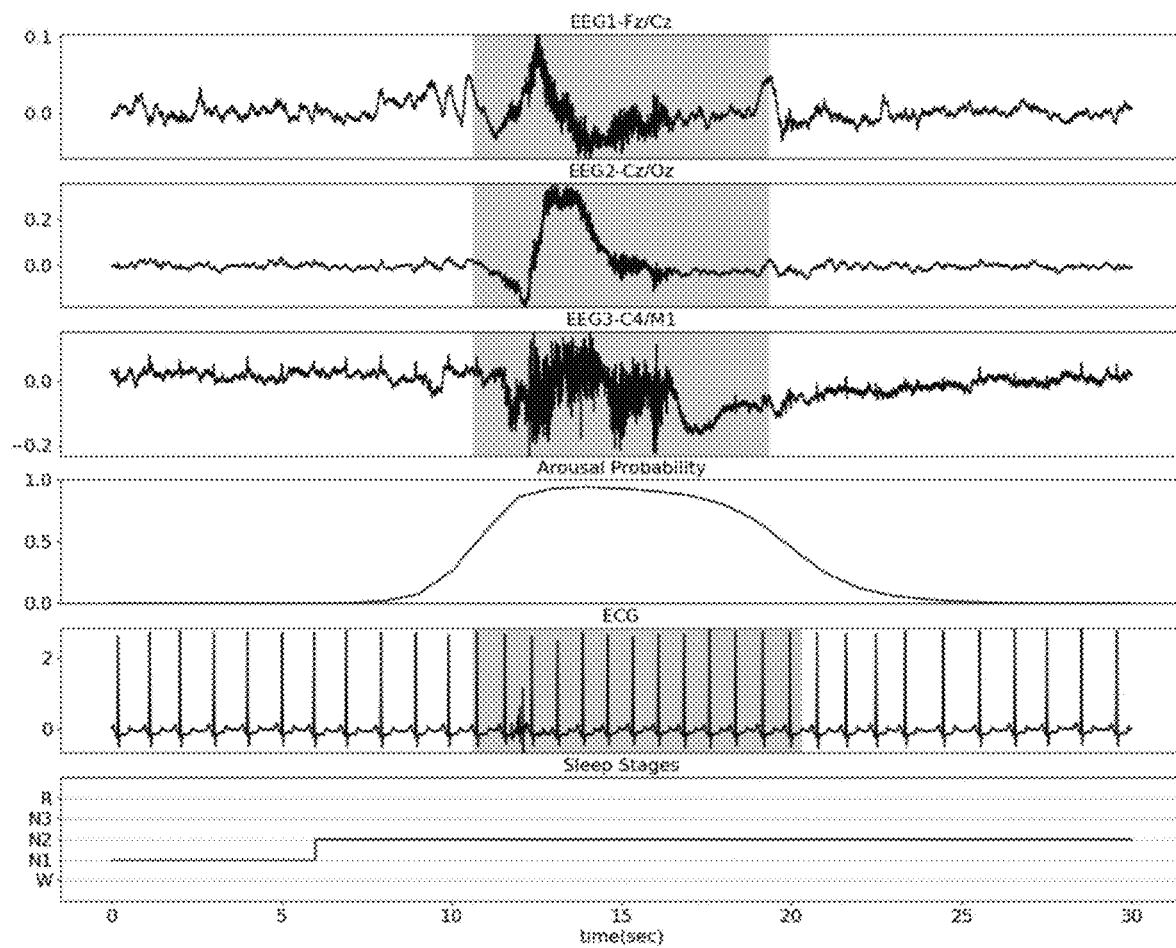
FIG. 8A is an illustrative example of a short arousal (<5 s) event from a participant with heart block. The shaded regions on the EEG derivations indicate manually scored ground truth arousal. The arousal probability indicates the outputs of the DeepCAD model. The shaded region on the ECG signal indicates detected arousal with a decision threshold of 0.4.
Figure 8B:
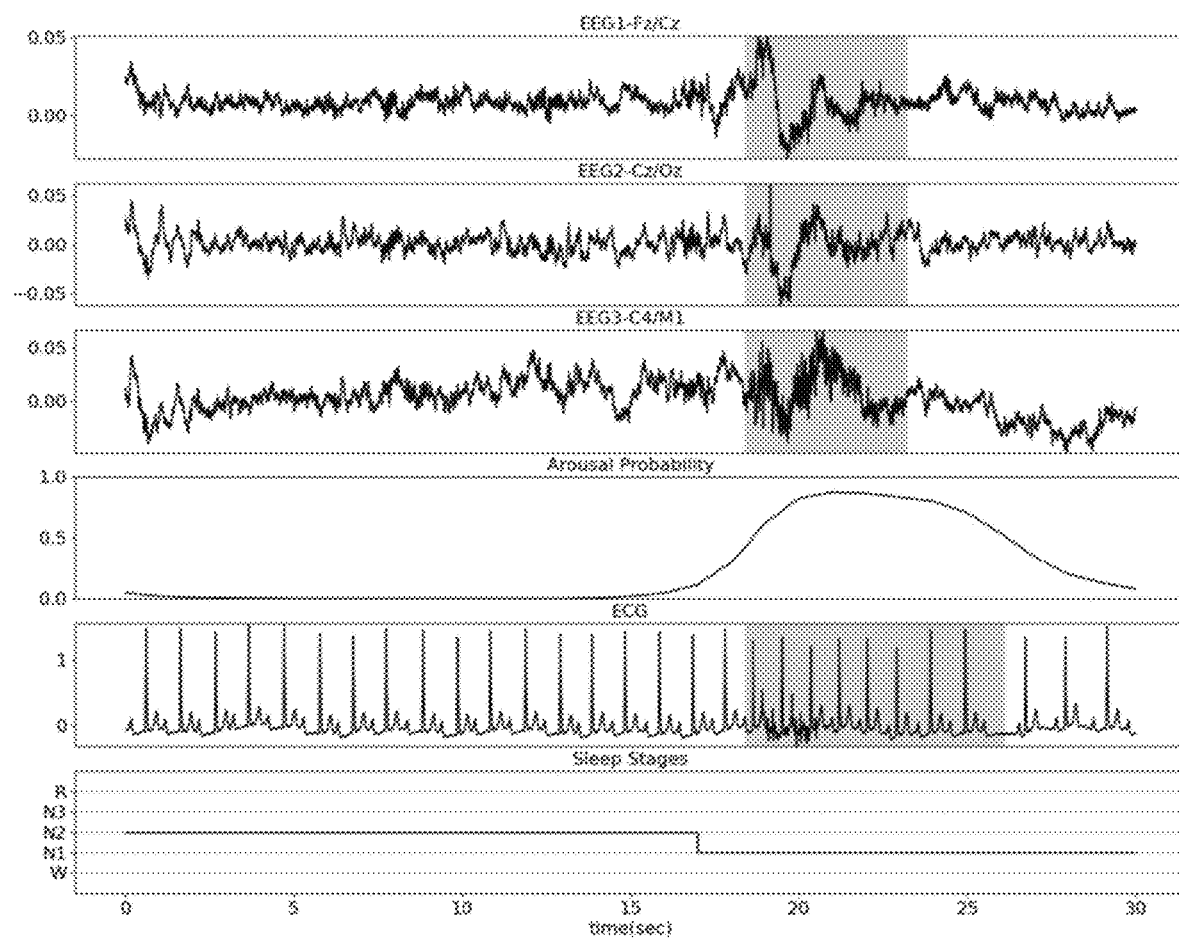
FIG. 8B is an illustrative example of a long arousal (>15 s) event.
Figure 8C:
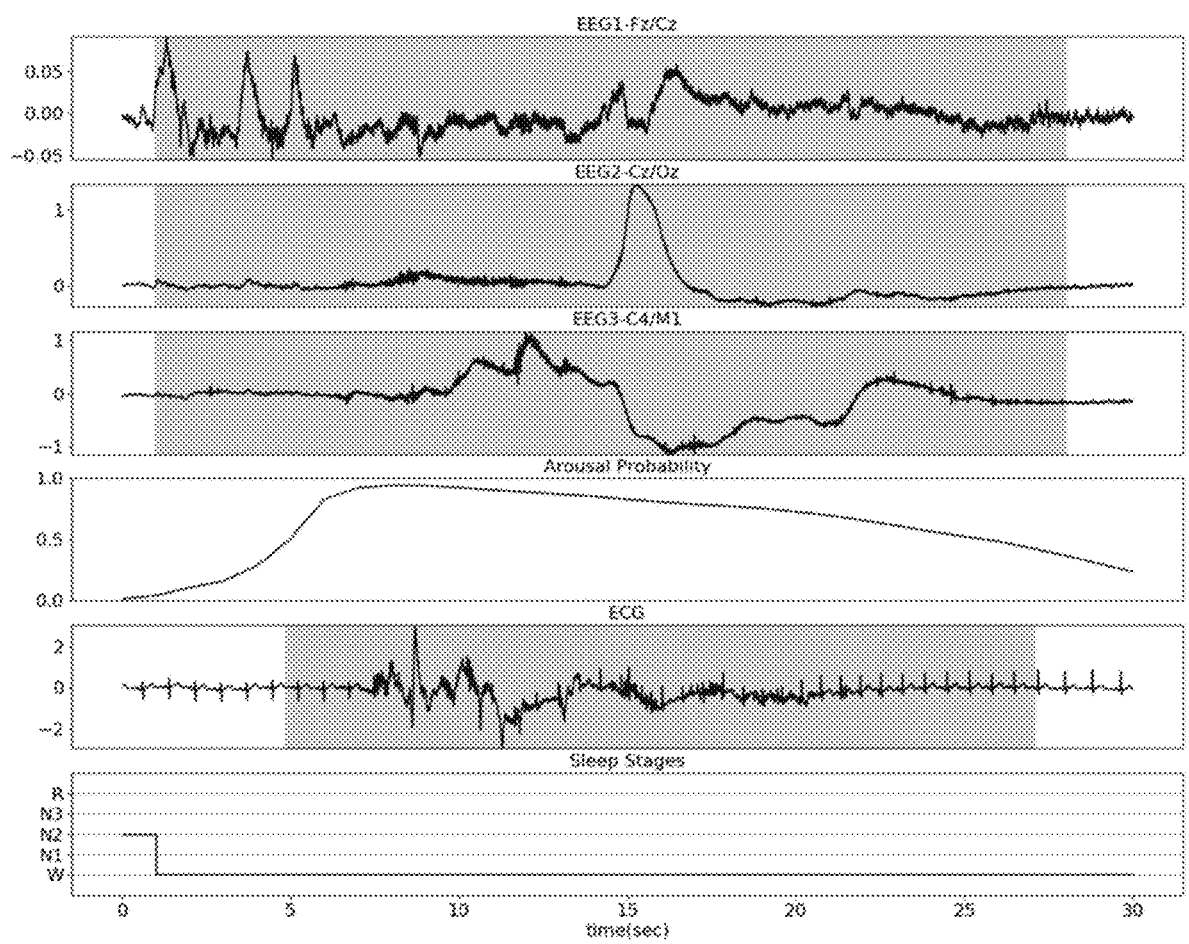
FIG. 8C is an illustrative example of a long arousal event (>15s) from a participant whose ECG signal included multiple types of noise (e.g., motion artifacts and EMG noise).

Illustrative Examples—FIG. 8A illustrates the detection of a typical arousal event. FIG. 8B illustrates the detection of a short arousal event (<5 s) in a participant with a heart rate abnormality (e.g. 2nd or 3rd degree block). FIG. 8C illustrates the detection of a long arousal event (>15 s) from a participant whose ECG signal included multiple types of noise. In the three illustrative examples, the probability of an arousal event is continuous, gradually increasing and gradually decreasing at the start and end of the event. Additionally, in the high arousal probability (>0.4) segment, the most noticeable ECG change is the shorter RR intervals.

Discussion—In this study, we developed and tested a deep learning model that can automatically detect cortical arousals using a single-lead ECG signal. The model was trained and tested on PSG records from a large database of unattended PSGs recorded from a diverse adult population. It was further evaluated using records from another large database of unattended PSGs. The deep learning model consisted of CNNs, RNNs, and a fully connected layer, and was capable of directly extracting features from a raw ECG signal and learning long-range dependencies in the extracted features. Compared to manually scored cortical arousal events as ground truth, the model attained a high level of accuracy.

The DeepCAD model has significant advantages over a RR interval-based algorithm. Such an algorithm needs a carefully designed preprocessing method for accurate annotation of R peaks. In contrast, our DeepCAD model learned to extract a large number of features from raw ECG signals. It required minimal data preprocessing and increased its precision as greater amounts of data were presented. It has the ability to handle ectopy and variability in arousal duration. Importantly, our algorithm can be applied on new data collected by different instruments.

Our DeepCAD model performed well in predicting arousals from a single-lead ECG. It obtained a 0.62 gross AUPRC on our test set (n=311) and a 0.81 correlation between the number of detected arousal events and the number of ground truth arousal events in a record-wise comparison. We also compared the model with several alternative models and demonstrated that the performance of the DeepCAD model was superior. Additionally, in the ablation study, we found the ResBlocks and LSTMs are the two components that were responsible for the biggest performance gain. By comparing the performance between the DeepCAD model and the model without LSTMs (InceptionBlock+ResBlocks), we believe capturing long-term ECG changes is an important capability for an accurate arousal detection model. Moreover, our end-to-end DeepCAD model can function without requiring experts' knowledge and derivations of the ECG signal. By utilizing the raw ECG signal as input, our method removes the pre-processing step that potentially loses useful information and introduces inconsistency to the final detection result. The four generalizability experiments using SHHS data further demonstrated that it was possible to replicate the performance of the DeepCAD model by simply training the model on new data without any hyper-parameter tuning. Compared with the directly applied DeepCAD model, the pretrained DeepCAD model only needed to be trained on a small dataset (10% of the full training set) to obtain a competitive performance. Additionally, training a pretrained model took significantly less time than training a random initialized model for achieving similar performance on SHHS data. These characteristics allow the DeepCAD model to have wider clinical applicability.

There are several caveats and limitations to our approach. First, although we excluded PSG records that were labeled as unreliable arousal annotation by scorers, the arousal annotation is only moderately reliable. Systematic differences existing in arousal scoring could have decreased performance of the deep learning model. Second, reporting exact event level sensitivity and precision are difficult because the detected arousal events on ECG and the cortical arousal on EEG signals may not always be synchronous. Third, we acknowledge that our deep learning model may have difficulty differentiating arousals from prolonged wakefulness and may identify arousals during epochs scored as wake. However, circumstances where there are repetitive transitions between wake and sleep are commonly scored as wake because sleep never constitutes more than 50% of any epoch. In these situations, the model will appropriately identify arousals in these epochs. In the future, it may be feasible to identify sleep/wakefulness and arousal using a single-lead ECG and a deep learning model that incorporates multi-task learning. Fourth, we did not classify the arousal events based on their etiology (e.g., respiratory or spontaneous). It is unclear whether a single-lead ECG signal contains sufficient information to make this differentiation. However, combining the DeepCAD model with an additional commonly used signal (e.g., pulse oximeter signal) may allow differential classification. Fifth, we acknowledge that the training time of our deep learning model is very long. However, the inference time is short. On average it needed less than 1.5 seconds to process one PSG record on a Nvidia RTX 2080Ti graphics card. Sixth, the presence of large amounts of ectopy on the ECG signal may adversely affect performance because of greater RR interval variability. However, our dataset did contain studies with ectopy which partially mitigated this source of error. Use of a training set with larger number of studies with ectopy will further increase the accuracy of the model. Finally, although we have demonstrated that it is feasible to use the arousal probability to identify cortical arousals from a single-lead ECG, conceptualizing the mid-level features of the deep learning model is challenging; the mid-layers' filters yield large amounts of output that are difficult to visualize. In the current study, we have attempted to present an example of one of our mid-layer outputs in FIG. 11B.

DeepCAD has several strengths. Most importantly, it only needs a single-lead ECG signal as input. Because a single ECG lead is easy to record in all environments, there is potentially wide applicability in a variety of clinical scenarios (e.g., home, intensive care, step down). In particular, it could be easily incorporated into the interpretation algorithms for Level III home sleep testing to facilitate identification of hypopneas associated only with arousals. The proposed end-to-end learning model also does not need complicated pre-processing and post-processing stages, has better generalizability, and has higher robustness. The DeepCAD model exhibited a competitive performance when tested on a large unattended PSG dataset, one that was recorded in a field type environment. As was shown in FIGS. 8A-8C, the end-to-end learning model has ability to capture the ECG pattern changes and detected arousal with arrhythmia and noisy ECG signals. Additionally, the DeepCAD-model-produced arousal probability can assist scorers in manual scoring. Furthermore, the generalizability experiments demonstrate that the DeepCAD model is applicable to new data collected by different hardware filters and sampling rates.

APPENDIX A

Figure 9:
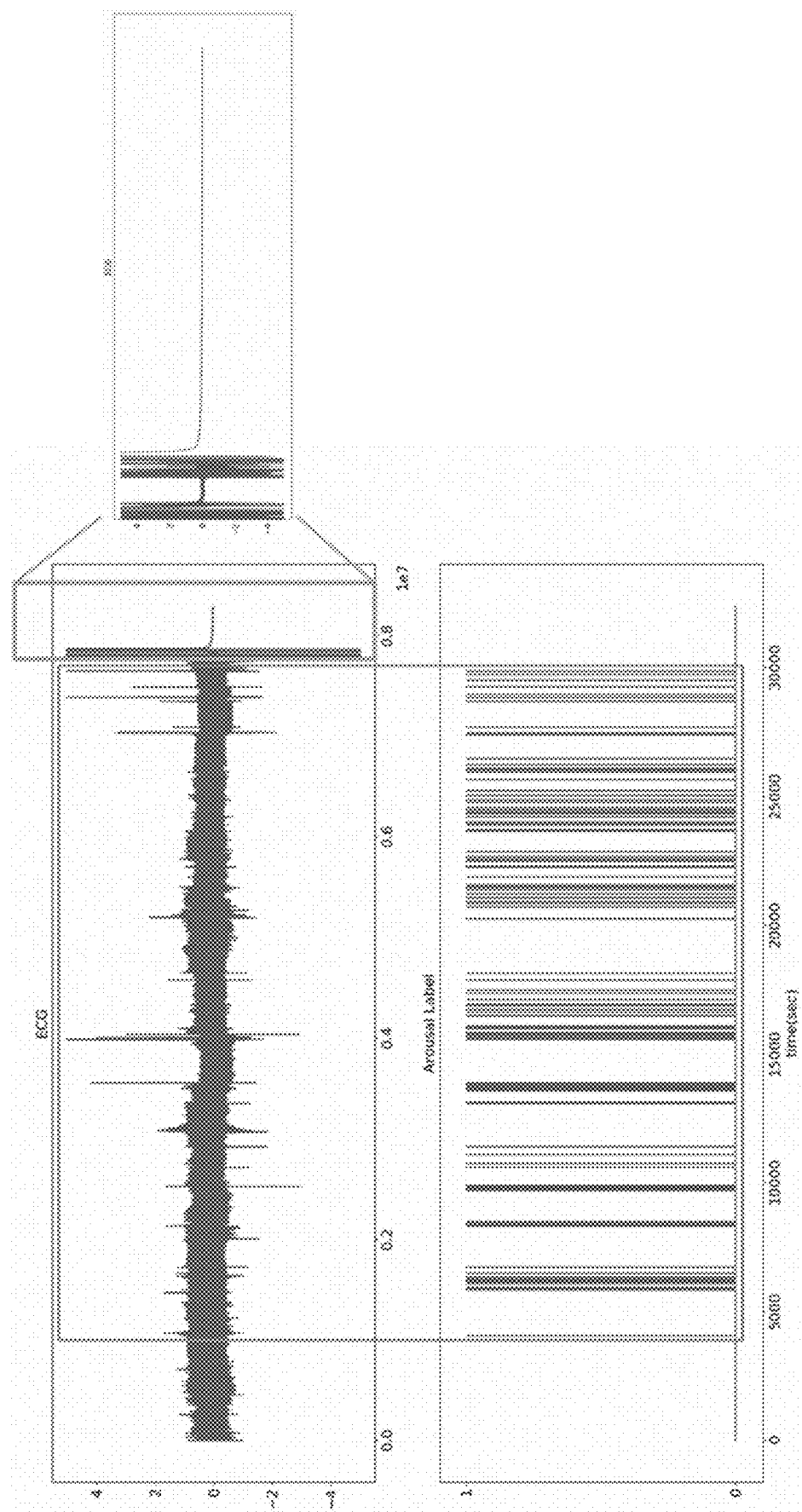
FIG. 9 illustrates segmentation of an ECG signal.

FIG. 9 shows a compressed one-night PSG record. In the Arousal Label graph, a value of 1 (i.e., a vertical line) indicates arousal present and a value of 0 (i.e., no vertical line) indicates arousal not present. The signals in the box are extracted from the one-night PSG record as the input sequence of the deep learning models. The segment starts from the 30 seconds before the first positive ground truth arousal label to the 30 seconds after the last positive ground truth arousal label.

APPENDIX B

Figure 10B:
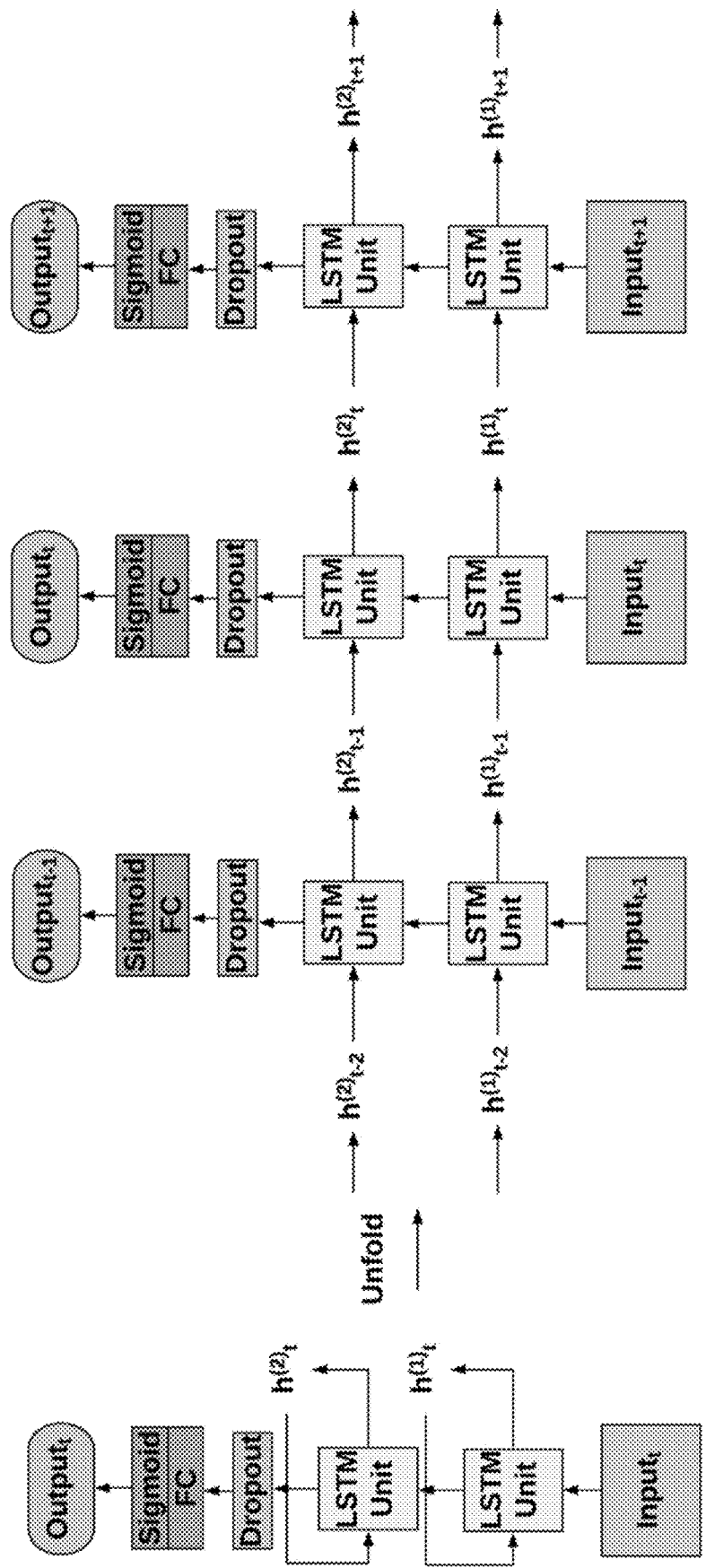
FIG. 10B shows the long short-term memory units (LSTMs) of FIG. 10A in more detail. Each LSTM is a type of recurrent neural network, where t is timestep and h is the hidden cells which pass the information from one timestep to the next timestep.
Figure 11A:
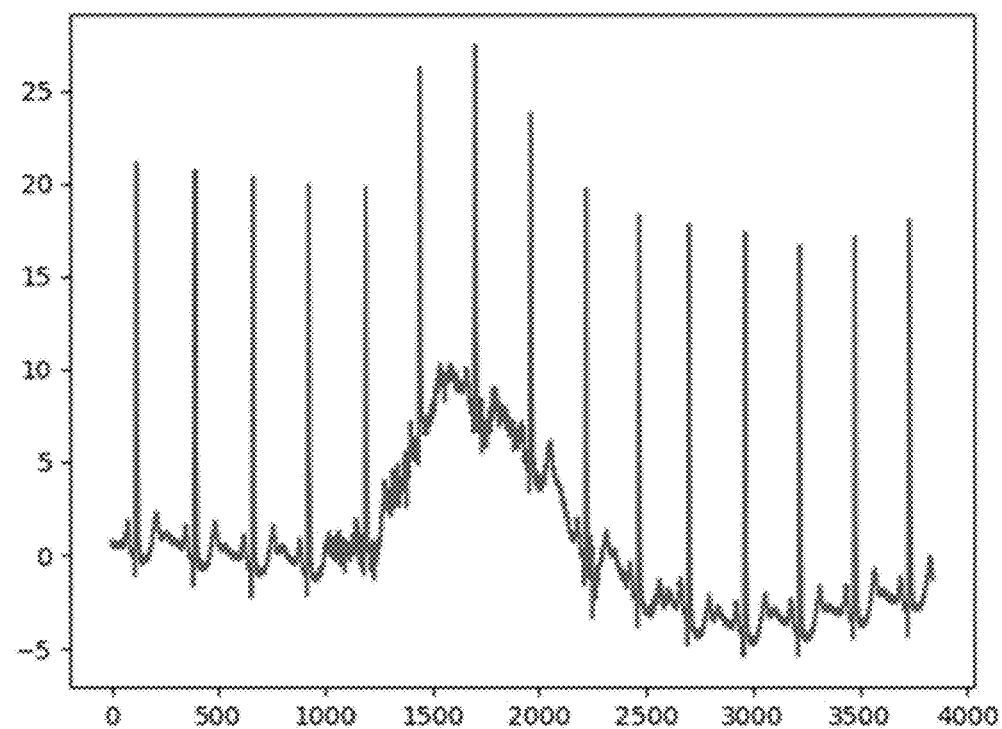
FIG. 11A shows a 256-Hz ECG signal with baseline noise drift.
Figure 11B:
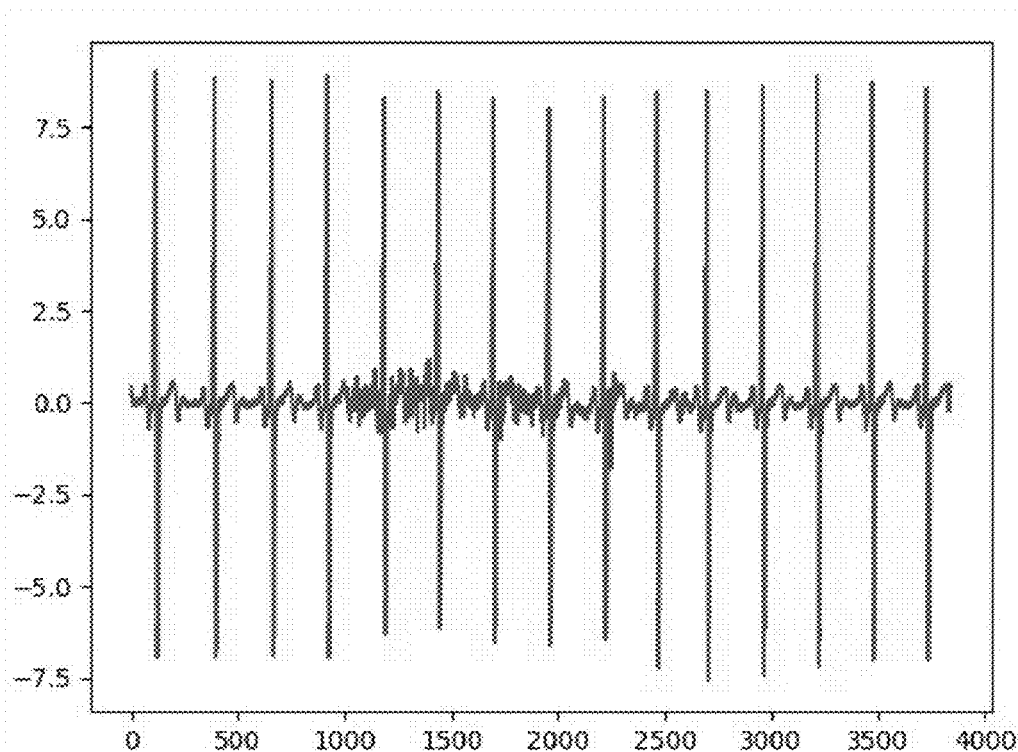
FIG. 11B shows one of the feature maps of the inception block. The output of the convolutional layer has removed the noise of the ECG signal in FIG. 11A.
Figure 12:
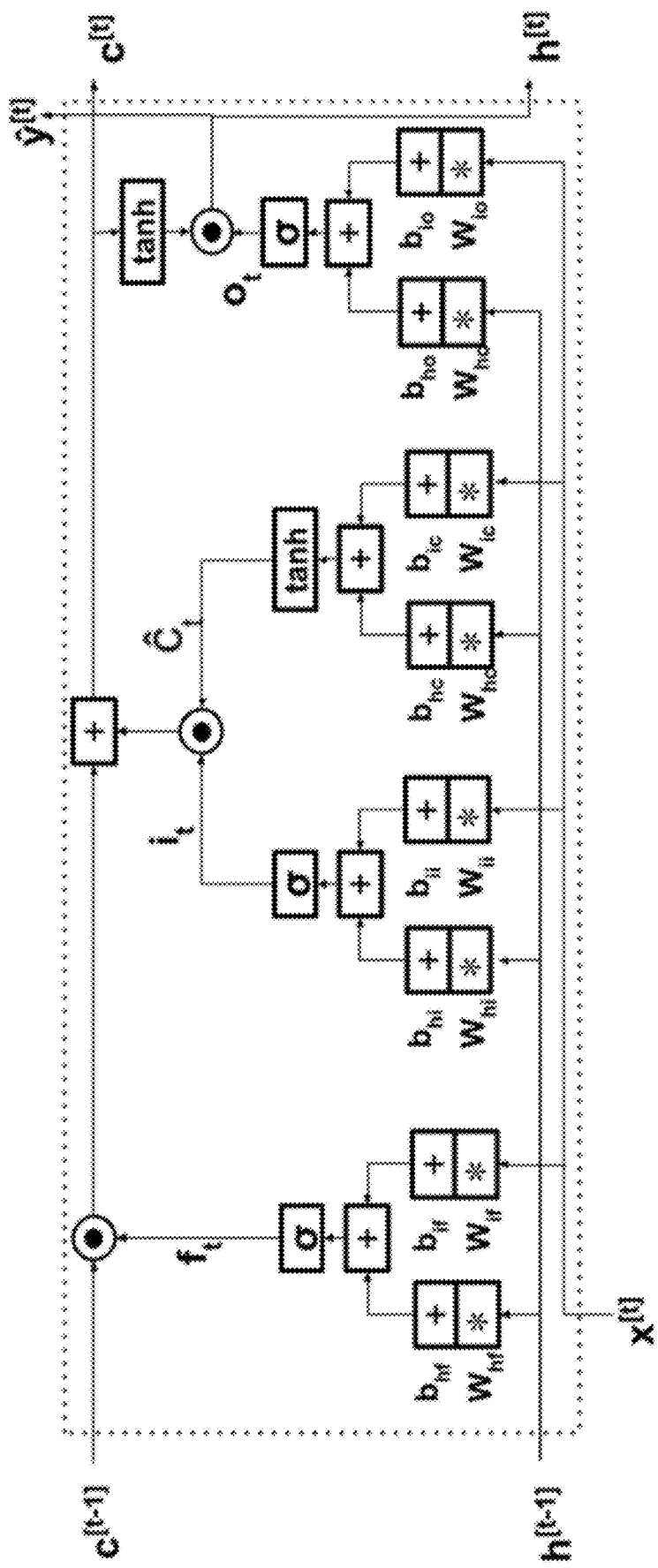
FIG. 12 is a functional diagram of a long short-term memory unit, where t represents timestep, and tanh and σ indicate the tanh and sigmoid functions, respectively. The labels b and w represent biases and weights, respectively, and h and c represent hidden cells and memory cells, respectively.

FIGS. 10A and 10B show the model architecture in more detail. Table 5 describes hyper-parameters. This model architecture is one example of the deep neural network 200 of FIG. 2. We specify the inception block as the first layer of the model. The comparison between the original ECG data and one of the feature maps of the inception block (the output of one filter) is shown in FIGS. 11A and 111B; the convolutional layer removes the baseline drift noise. Then, we use the pre-activated ResBlocks to extract features from ECG data and downsample the ECG data from 256 Hz to 1 Hz. The convolutional layers have 32 k filters where k starts from one and increases by one in pre-activation ResBlock two. Except for the first convolution of pre-activation ResBlock two, all outputs of convolutions have the same length as the original input. In pre-activation ResBlock two, we used the first convolutional layer with a stride of two to downsample the ECG signal. As suggested by in the above references by He et al, we only use a direct connection as a shortcut. In pre-activation ResBlock two, we employed an average pooling layer with a stride of two as a shortcut. The average pooling smoothed signal propagation. In the model, we used batch normalization after each convolution layer to normalize the data, which can increase training speed and make the model more robust. We also used a rectified linear unit activation function after each batch normalization layer. We applied the two pre-activated ResBlocks structure eight times before the data were passed to the LSTMs. A LSTM layer employs a recurrent structure for passing the information from previous timesteps to the current timestep (see FIG. 10B). The LSTM units are memory cells that store temporal information for a short time and include gating components that control the flow of the content being stored. Three sigmoidal gates, including a forget gate (f), an input gate (i), and an output gate (o), control access to the memory cells. The forget gate (see Eqn. 1) decides what information needs to be removed from the memory cells. The input gate (see Eqn. 2) decides what information needs to be updated in the memory cells. The memory cell state is updated according to Eqns. 3 and 4, where * is the Hadamard (elementwise) product. The output gate provides the filtered memory cell state by Eqns. 5 and 6. The inputs of one LSTM unit includes the outputs of the previous LSTM unit and extracted ECG features. We used a dropout with a rate of 0.2 between the highest LSTM layer and the fully connected layer. The fully connected layer with a sigmoid function produced the probability of arousal presence. The output of the DeepCAD model was a sequence of probability of arousal presence for each second.

$$f_t = \sigma(W_{hf} h_{t-1} + b_{hf} + W_{if} x_t + b_{if}) \quad (1)$$

$$i_t = \sigma(W_{hi} h_{t-1} + b_{hi} + W_{ii} x_t + b_{ii}) \quad (2)$$

$$\hat{c}_t = \tanh(W_{hc} h_{t-1} + b_{hc} + W_{ic} x_t + b_{ic}) \quad (3)$$

$$c_t = f_t * c_{t-1} + i_t * \hat{c}_t \quad (4)$$

$$o_t = \sigma(W_{ho} h_{t-1} + b_{ho} + W_{io} x_t + b_{io}) \quad (5)$$

$$\hat{y}_t = h_t = o_t * \tanh(c_t) \quad (6)$$

TABLE 5

Model hyper-parameters

| | Filters/Hidden Cells | Kernel | Stride |
|---|---|---|---|
| Inceptionblock (Conv1) | 8 | 11 | 1 |
| Inceptionblock (Conv2) | 8 | 15 | 1 |
| Inceptionblock (Conv3) | 8 | 19 | 1 |
| Inceptionblock (Conv4) | 8 | 23 | 1 |
| ResBlock One (Conv1) | 32k | 1 | 1 |
| ResBlock One (Conv2) | 32k | 7 | 1 |
| ResBlock Two (Conv1) | 32k | 2 | 2 |
| ResBlock Two (Conv2) | 32k | 7 | 1 |
| ResBlock Two (AveragePooling) | 32k | 2 | 2 |
| LSTM1 | 256 | — | — |
| LSTM2 | 256 | — | — |
| FC | 1 | — | — |

APPENDIX C

In this study, we also developed an alternative model (Spectrogram+LSTMs) that used spectrogram and long short-term memory (LSTMs). We used a non-overlapped Hann taper function with a window size of 256 to compute the spectrogram that extracted frequency information from a sequence of ECG data. Then, we passed the spectrogram features to two layers of LSTMs followed by a fully-connected layer with sigmoid activation function. We also used a dropout between the highest LSTM layer and the fully-connected layer. The final output was the probability of arousal presence. We evaluated the performance of this model on the test set.

In addition, we conducted ablation experiments for the proposed cortical arousal detection model by testing four simplified models. In the LSTMs model, two LSTM layers were used to extract temporal features followed by a fully-connected layer to predict the probability of the presence of arousal. We used dropout between the LSTM layer and the fully-connected layer. The InceptionBlock+LSTMs model consisted of one inception block layer, two LSTM layers and a fully-connected layer. The ResBlocks+LSTMs model consisted of a ResBlocks layer, two LSTM layers, and a fully-connected layer. The InceptionBlock+ResBlocks model consisted of one inception-block layer, ResBlocks layer, and a fully-connected layer. The output of Inception-Block+ResBlocks model is a probability of arousal. We used the same hyper-parameters in the four models as proposed with DeepCAD model. We tested performance of the simplified models on the MESA test set (n=311) and reported the results in Table 2.

APPENDIX D

Figure 15:
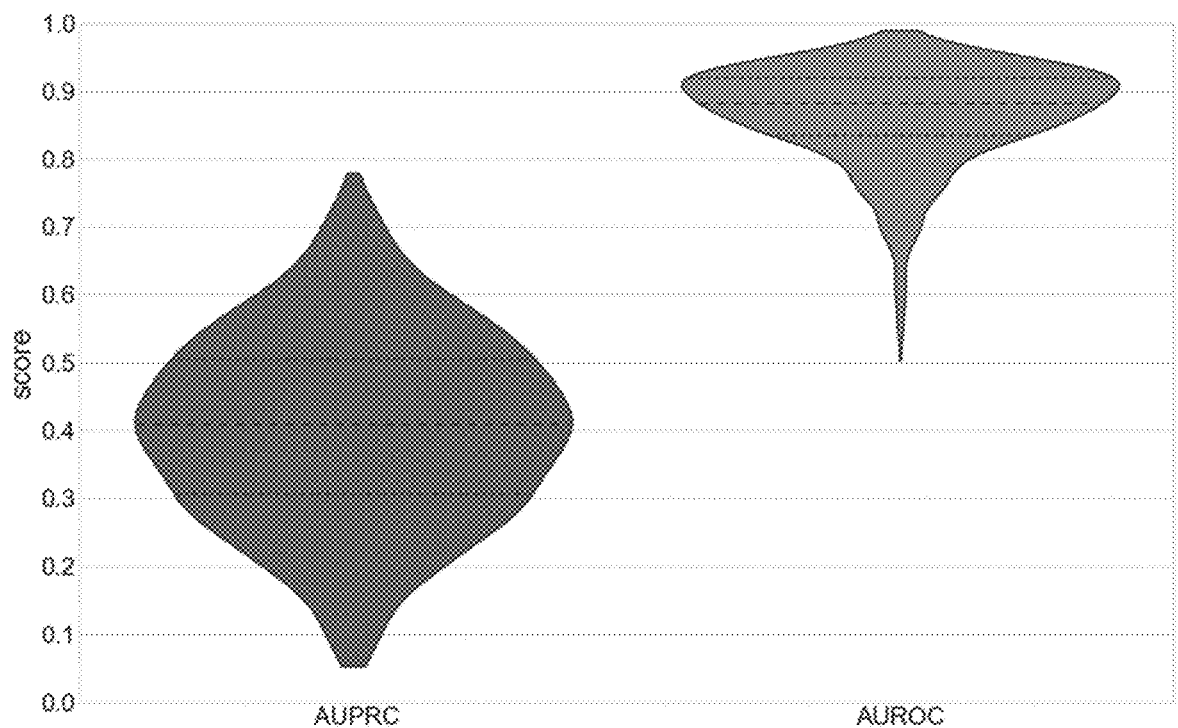
FIG. 15 illustrates record-wise performance of the pre-trained DeepCAD model.
Figure 16:
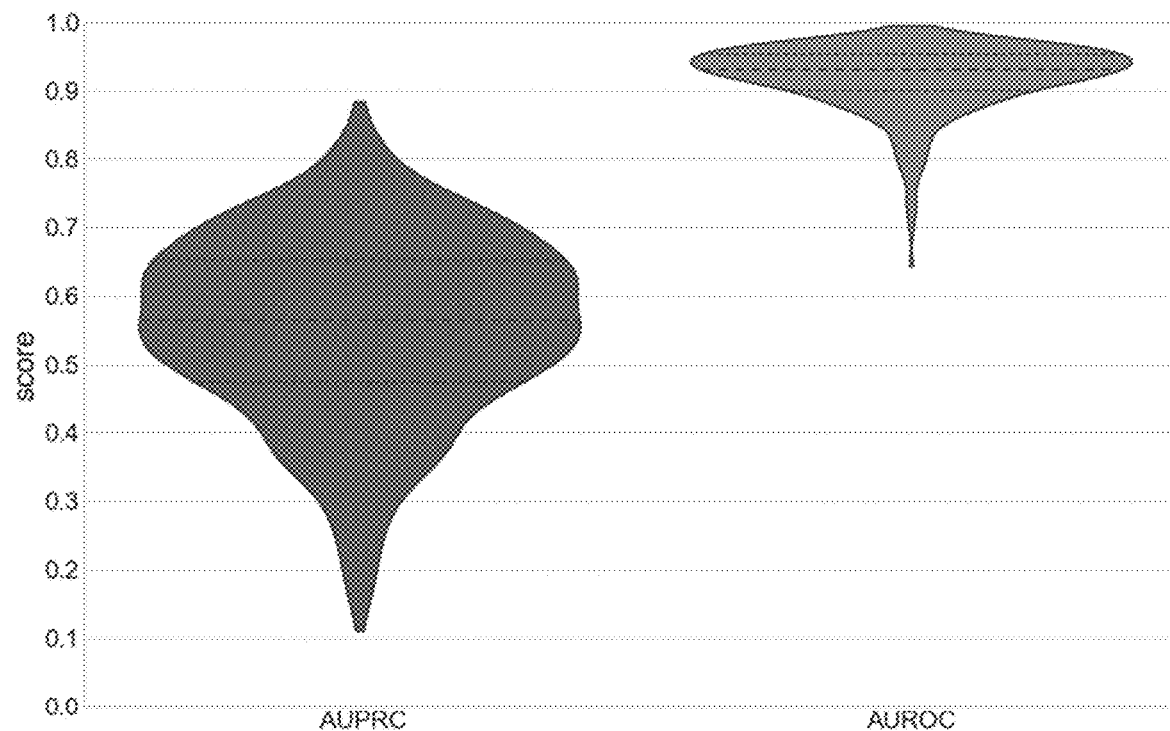
FIG. 16 illustrates record-wise performance of the model that was trained on sleep heart health study data.
Figure 17:
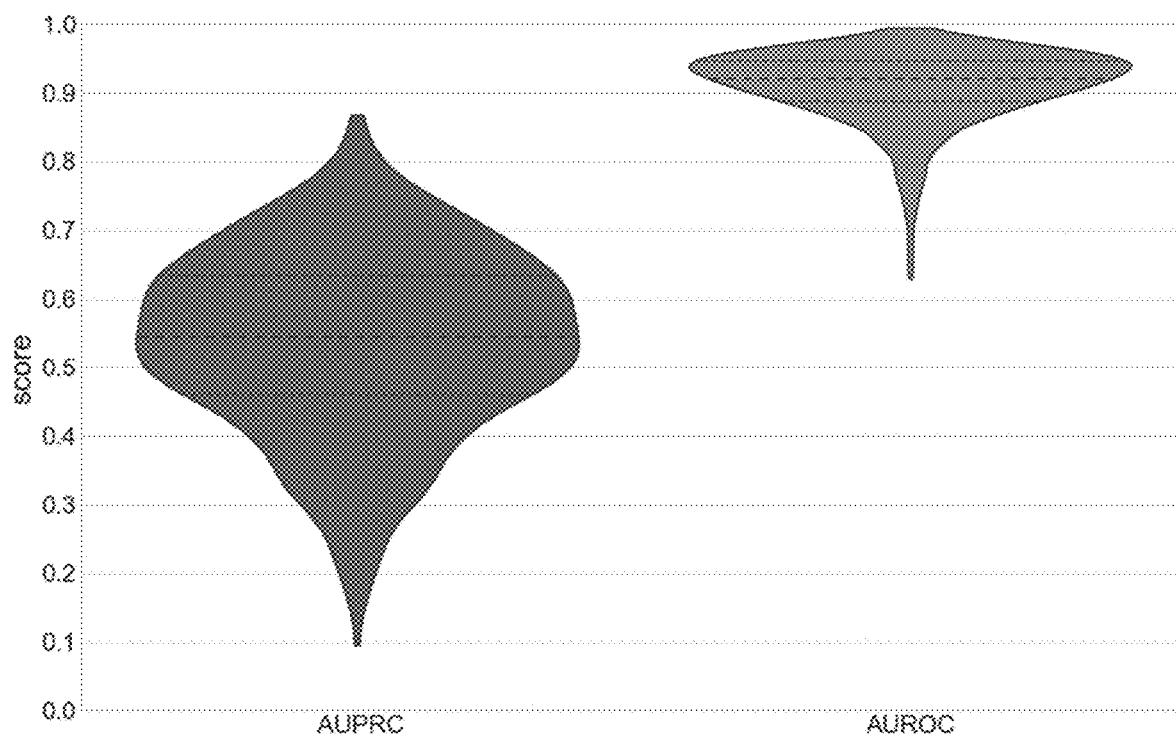
FIG. 17 illustrates record-wise performance of the pre-trained DeepCAD model that was additionally trained on 105 SHHS records.
Figure 18:
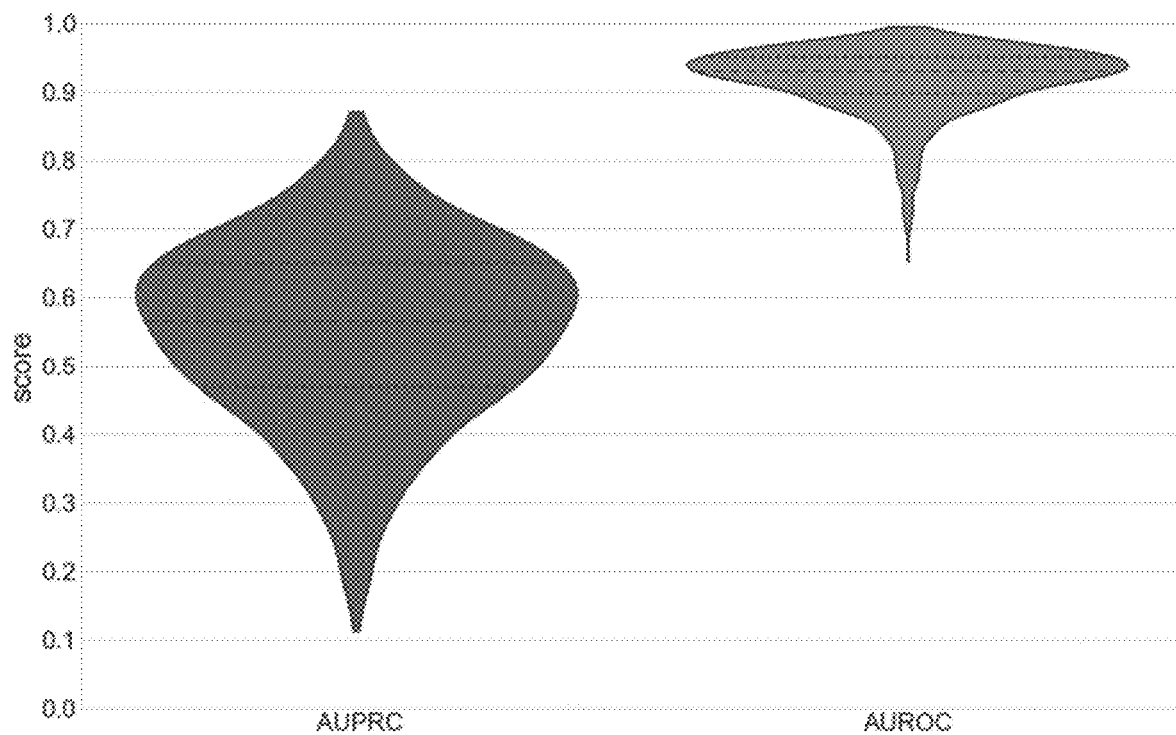
FIG. 18 illustrates record-wise performance of the pre-trained DeepCAD model that was additionally trained on 1058 SHHS records.

FIGS. 15-18 show the record-wise AUPRC scores of the four models. The models exhibited widely different performance across SHHS test records (n=785). FIG. 15 shows the AUPRC and AUROC ranges of the directly applied model are 0.05-0.78 and 0.50-0.99, respectively. The median of AUPRC is 0.40 and the median of AUROC is 0.88. FIG. 16 shows the AUPRC and AUROC ranges of the model that was trained on the SHHS training set (n=1058) are 0.11-0.88 and 0.64-0.99. The median of AUPRC is 0.57 and the median of AUROC is 0.93. FIG. 17 represents the record-wise performance of the pretrained model that was additionally trained on a part of SHHS training set (n=105); there were AUPRC scores of 0.09-0.87 with a median of 0.55 and AUROC scores of 0.63-0.99 with a median of 0.92. The pretrained model that was additionally trained on the full SHHS training set (n=1058) produced AUPRC scores of 0.11-0.87 with a median of 0.57 and AUROC of 0.65-1.00 with a median of 0.93 (see FIG. 18).

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An electrocardiography monitor, comprising:
   a processor;
   a memory communicably coupled with the processor, the memory storing a deep neural network comprising:
   an inception module comprising a plurality of convolutional neural networks (CNNs);
   a residual neural network configured to downsample by a downsampling stride that is greater than one;
   a feedback path connecting an output of the residual neural network to an input of the residual neural network; and
   a long short-term memory (LSTM) neural network; and
   an electronic display communicably coupled with the processor;

the memory further storing machine-readable instructions that, when executed by the processor, control the ECG monitor to:
filter a sequence of ECG values with the inception module such that the plurality of CNNs process the sequence of ECG values in parallel, each of the plurality of CNNs outputting a respective one of a plurality of feature maps;
iteratively downsample, with the residual neural network and via the feedback path, the plurality of feature maps to generate a respective plurality of downsampled feature maps;
calculate a sequence of cortical-arousal probabilities by feeding the plurality of downsampled feature maps into the LSTM neural network;
compare each of the sequence of cortical-arousal probabilities to a threshold; and
display, on the electronic display, an indication in response to one or more of the sequence of cortical-arousal probabilities exceeding the threshold.

2. The ECG monitor of claim 1, further comprising a single-lead ECG configured to generate the sequence of ECG values.

3. The ECG monitor of claim 1, the inception module comprising a concatenator configured to concatenate the plurality of feature maps to form a channel array.

4. The ECG monitor of claim 1, wherein:
the inception module further includes a window function configured to process the sequence of ECG values into a spectrogram; and
the plurality of feature maps includes at least part of the spectrogram.

5. The ECG monitor of claim 1, the residual neural network including a fully pre-activated downsampling residual unit having:
a downsampling CNN configured to process the plurality of feature maps with the downsampling stride;
a shortcut pooling layer configured to bypass the downsampling CNN and to pool the plurality of feature maps by the downsampling stride; and
a downsampling adder configured to add an output of the downsampling CNN and an output of the shortcut pooling layer.

6. The ECG monitor of claim 5, the residual neural network further including, prior to the fully pre-activated downsampling residual unit, a fully pre-activated non-downsampling residual unit having:
a non-downsampling CNN configured to process the plurality of feature maps with a stride of one;
a shortcut connection configured to bypass the non-downsampling CNN; and
a non-downsampling adder configured to add an output of the non-downsampling CNN and an output of the shortcut connection.

7. The ECG monitor of claim 1, the LSTM neural network including a sequence of memory cells.

8. The ECG monitor of claim 7, wherein:
each memory cell of the sequence of memory cells has an input cell state and an output cell state, the output cell state being connected to the input cell state of a next memory cell of the sequence of memory cells; and
the machine-readable instructions that, when executed by the processor, control the ECG monitor to calculate the sequence of cortical-arousal probabilities include machine-readable instructions that, when executed by the processor, control the ECG monitor to:
feed the plurality of downsampled feature maps into the input cell state of a first memory cell of the sequence of memory cells; and
calculate the sequence of cortical-arousal probabilities based on the output cell state of a last memory cell of the sequence of memory cells.

9. The ECG monitor of claim 7, the LSTM neural network including:
a fully-connected layer connected to an output of the sequence of memory cells; and
a nonlinear layer connected to an output of the fully-connected layer.

10. An electrocardiography method, comprising:
filtering, with an inception module of a deep neural network, a sequence of ECG values such that a plurality of convolutional neural networks (CNNs) of the inception module process the sequence of ECG values in parallel, each of the plurality of CNNs outputting a respective one of a plurality of feature maps;
iteratively downsampling, with a residual neural network of the deep neural network and via a feedback path that connects an output of the residual neural network to an input of the residual neural network, the plurality of feature maps to generate a respective plurality of downsampled feature maps, the residual neural network having a downsampling stride that is greater than one;
calculating a sequence of cortical-arousal probabilities by feeding the plurality of downsampled feature maps into a long short-term memory (LSTM) neural network of the deep neural network;
comparing each of the sequence of cortical-arousal probabilities to a threshold; and
displaying, on an electronic display, an indication in response to one or more of the sequence of cortical-arousal probabilities exceeding the threshold.

11. The ECG method of claim 10, further comprising sensing the sequence of ECG values with a single-lead ECG sensor.

12. The ECG method of claim 10, wherein said filtering comprises concatenating the plurality of feature maps to create a channel array.

13. The ECG method of claim 10, wherein said filtering further includes applying a window function of the inception module to the sequence of ECG values to create a spectrogram, the plurality of feature maps including at least part of the spectrogram.

14. The ECG method of claim 10, wherein said iteratively downsampling includes iteratively downsampling the plurality of feature maps with a fully pre-activated downsampling residual unit of the residual neural network, the fully pre-activated downsampling residual unit having:
a downsampling CNN that processes the plurality of feature maps with the downsampling stride;
a shortcut pooling layer that bypasses the downsampling CNN and pools the plurality of feature maps by the downsampling stride; and
a downsampling adder that adds an output of the downsampling CNN and an output of the shortcut pooling layer.

15. The ECG method of claim 14, wherein said iteratively downsampling further includes iteratively downsampling the plurality of feature maps with a fully pre-activated non-downsampling residual unit of the residual neural network, the fully pre-activated non-downsampling residual unit having:
a non-downsampling CNN that processes the plurality of feature maps with a stride of one;

a shortcut connection that bypasses the non-downsampling CNN; and a non-downsampling adder that adds an output of the non-downsampling CNN and an output of the shortcut connection.

16. The ECG method of claim 10, wherein said calculating includes calculating the sequence of cortical-arousal probabilities with a sequence of memory cells of the LSTM neural network.

17. The ECG method of claim 16, wherein said calculating the sequence of cortical-arousal probabilities with the sequence of memory cells includes:

feeding the plurality of downsampled feature maps into an input cell state of a first memory cell of the sequence of memory cells;

passing an output cell state of each memory cell of the sequence of memory cells to an input cell state of a next memory cell of the sequence of memory cells; and calculating the sequence of cortical-arousal probabilities based on an output cell state of a last memory cell of the sequence of memory cells.

18. The ECG method of claim 16, wherein said calculating further includes:

passing an output of the sequence of memory cells to an input of a fully-connected layer; and passing an output of the fully-connected layer to an input of a nonlinear layer.

* * * * *